(12) United States Patent
Almstead et al.

(10) Patent No.: US 6,878,729 B2
(45) Date of Patent: Apr. 12, 2005

(54) MEDICINAL USES OF DIHYDROPYRAZOLES

(75) Inventors: Ji-In Kim Almstead, Holmdel, NJ (US); Nicholas John Izzo, Pittsburgh, PA (US); David Robert Jones, Milford, OH (US); Richard Masaru Kawamoto, Lebanon, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 59 days.

(21) Appl. No.: 10/134,873

(22) Filed: Apr. 29, 2002

(65) Prior Publication Data

US 2003/0083351 A1 May 1, 2003

Related U.S. Application Data

(60) Provisional application No. 60/288,720, filed on May 4, 2001.

(51) Int. Cl.[7] .................. A61K 31/4439; C07D 401/04
(52) U.S. Cl. ..................... 514/341; 546/275.4; 514/341
(58) Field of Search ....................... 546/275.4; 514/341

(56) References Cited

U.S. PATENT DOCUMENTS

| | | | |
|---|---|---|---|
| 3,947,583 | A | 3/1976 | Berenson |
| 4,997,835 | A | 3/1991 | Schaper et al. |
| 5,073,492 | A | 12/1991 | Chen et al. |
| 5,084,458 | A | 1/1992 | Schaper et al. |
| 5,194,596 | A | 3/1993 | Tischer et al. |
| 5,219,739 | A | 6/1993 | Tischer et al. |
| 5,283,341 | A | 2/1994 | Tanaka et al. |
| 5,882,914 | A | 3/1999 | Semenza |
| 5,985,913 | A | 11/1999 | Williams et al. |
| 6,020,462 | A | 2/2000 | Semenza |
| 6,291,505 | B1 * | 9/2001 | Huebner et al. ............ 514/406 |

FOREIGN PATENT DOCUMENTS

| | | |
|---|---|---|
| DE | 19904391 A1 | 8/2000 |
| WO | WO 92/19615 | 11/1992 |
| WO | WO 98/56377 A1 | 12/1998 |
| WO | WO 99/58523 | 11/1999 |
| WO | WO 99/62884 | 12/1999 |
| WO | WO 00/10578 A1 | 3/2000 |
| WO | WO 00/45894 A2 | 8/2000 |
| WO | WO 00/76503 A1 | 12/2000 |

OTHER PUBLICATIONS

Bun et al., "Oxygen Sensing and Molecular Adaptation of Hypoxia", *Amer. Physiological Society*, 1996, pp. 839–885, vol. 76, No. 3.

Semenza, "Regulation of Mammalian $O_2$ Homeostasis by Hypoxia–Inducible Factor 1.", *Annu. Rev. Cell Dev. Biol.*, 1999, pp. 551–578, vol. 15.

Shweiki et al., "Induction of vascular endothelial growth factor expression by hypoxia and by glucose deficiency in multicell spheroids: Implications for tumor angiogenesis", *Proc. Natl. Acad. Sci.*, 1995, pp. 768–772, vol. 92.

Semenza, "HIF–1: mediator of physiological and pathophysiological responses to hypoxia", *J. Appl. Physiol.*, 2000, pp. 1474–1480, vol. 88.

Semenza, "Hypoxia–inducible factor 1: master regulator of $O_2$ homeostasis", *Genetics & Development*, 1998, pp. 588–594, vol. 8.

Jiang et al., "Transactivation and inhibitory domanins of hypoxia–inducible factor $1\alpha$", *J. Biol. Chem.*, 1997, pp. 19253–19260, vol. 272, No. 31.

Jiang et al., "Dimerization, DNA binding, and transactivation properties of hypoxia–inducible factor 1", *J. of Biol. Chem.*, 1996, pp. 17771–17778, vol. 271, No. 30.

Pearlman et al., "Magnetic resonance mapping demonstrates benefits of VEGF–induced myocardial angiogenesis", *Nature Medicine*, 1995, pp. 1085–1089, vol. 1, No. 10.

Takeshita et al., "A single intraarterial bolus of vascular endothelial growth factor augments revascularization in a rabbit ischemic hind limb model", *J. Clin. Invest.*, 1994, pp. 662–670, vol. 93.

Hendel et al., "Effect of intracoronary recombinant human vascular endothelial growth factor on myocardial perfusion", *Circulation*, 2000, pp. 118–121, vol. 101, No. 2.

Schwartz et al., "Evaluation of the effects of intramyocardial injection of DNA expressing vascular endothelial growth factor (VEGF) in a myocardial infarction mdoel in the rat—angiogenesis and angioma formation", *J. Amer. College of Cardiology*, 2000, pp. 1323–1330, vol. 35, No. 5.

Shweiki et al., "Vascular endothelial growth factor induced by hypoxia may mediate hypoxia–initiated angiogenesis", *Letters to Nature*, 1992, pp. 843–845, vol. 359.

Levy et al., "Transcriptional regulation of the rat vascular endothelial growth facror gene by hypoxia", *Drug Disc. Today*, 1995, pp. 13333–13340, vol. 270, No. 22.

Ikeda et al., "Hypoxia–induced transcriptional activation and increased mRNA stability of vascular endothelial growth factor in C6 glioma cells", *J. Biol. Chem.*, 1995, pp. 19761–19766, vol. 270, No. 34.

Levy et al., "Post–transcriptional regulation of vascular endothelial growth factor by hypoxia", *Drug Disc Today*, 1996, pp. 2746–2753, vol. 271, No. 5.

(Continued)

Primary Examiner—Ceila Chang
Assistant Examiner—Janet L Coppins
(74) Attorney, Agent, or Firm—David V. Upite; Andrew A. Paul

(57) ABSTRACT

Compounds having a structure according to Formula (I):

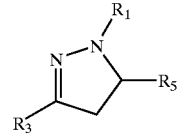

Formula (I)

are effective in a method of increasing erythropoietin and vascularization of tissue in a subject in need thereof.

4 Claims, No Drawings

OTHER PUBLICATIONS

Agani et al., "Mersalyl is a novel inducer of vascular endothelial growth factor gene expression and hypoxia-inducible factor 1 activity", *Mol. Pharmacol.*, 1998, pp. 749–754, vol. 54.

Brogi et al., "Indirect angiogenic cytokines upregulate VEGF and bFGF gene expression in vascular smooth muscle cells, whereas hypoxia upregulates VEGF expression only", *Circulation*, 1994, pp. 649–652, vol. 90.

Van Belle et al., "Potentiated angiogenic effect of scatter factor/hepatocyte growth factor via induction of vascular endothelial growth factor", *Circulation*, 1998, pp. 381–390, vol. 97. No. 4.

Semenza, "Regulation of erythropoietin production", *Hematol. Oncol., Clin. N. Amer.*, 1994, pp. 863–885, vol. 8, No. 5.

Semenza et al., "Transcriptional regulation of genes encoding glycolytic enzymes by hypoxia–inducible factor 1", *J. Biol. Chem.*, 1994, pp. 23757–23763, vol. 269, No. 38.

Kranz, "Blood", *J. of Amer. Society of Hematology*, 1991, pp. 419–434, vol. 77, No. 3.

Quroshi et al., "Minicry of erythropoietin by a nonpeptide molecule", *PNAS*, 1999, pp. 12156–12161, vol. 96, No. 21.

Manna et al., "Inhibitory Effect of 1,3,5–Triphenyl–4,–5–Dihydro–(1H)–Pyrazole Derivatives on Activity of Amine Oxidases", *J. Enzyme Inhibition*, 1998, pp. 207–216, vol. 13.

Rao et al., "Synthesis and ANTIMICROBIAL Activity of Some New 1,8–NAPH–Thyridines", *Indian J. of Heterocyclic Chem.*, 1995, pp. 211–214, vol. 4.

Bilgin et al., "Some 1,3,5–Triphenyl–2–Pyrazolines with Antidepressant Activities", *Database CA online, Chemical Abstracts Service, Columbus, Ohio, US*, Accession No. 120:235419 XP002206884, Abstract.

* cited by examiner

SEQUENCE LISTING

```
<160> NUMBER OF SEQ ID NOS: 24

<210> SEQ ID NO 1
<211> LENGTH: 23
<212> TYPE: DNA
<213> ORGANISM: Homo sapiens

<400> SEQUENCE: 1
accctggctt tactgctgta cct                                              23

<210> SEQ ID NO 2
<211> LENGTH: 22
<212> TYPE: DNA
<213> ORGANISM: Homo sapien

<400> SEQUENCE: 2
tgggacttct gctctccttc tg                                               22

<210> SEQ ID NO 3
<211> LENGTH: 22
<212> TYPE: DNA
<213> ORGANISM: Homo sapien

<400> SEQUENCE: 3
accatgccaa gtggtcccag gc                                               22

<210> SEQ ID NO 4
<211> LENGTH: 28
<212> TYPE: DNA
<213> ORGANISM: Homo sapien

<400> SEQUENCE: 4
gtagacagat gttggtgcaa tacaagta                                         28

<210> SEQ ID NO 5
<211> LENGTH: 26
<212> TYPE: DNA
<213> ORGANISM: Homo sapien

<400> SEQUENCE: 5
caatacctgt taccagcaca gaaact                                           26

<210> SEQ ID NO 6
<211> LENGTH: 31
<212> TYPE: DNA
<213> ORGANISM: Homo sapien

<400> SEQUENCE: 6
actacagtca aacatgcgct gtgagaagct g                                     31

<210> SEQ ID NO 7
<211> LENGTH: 25
<212> TYPE: DNA
<213> ORGANISM: Homo sapien

<400> SEQUENCE: 7
gctcttgtga cagcaaagat aacaa                                            25

<210> SEQ ID NO 8
<211> LENGTH: 16
<212> TYPE: DNA
<213> ORGANISM: Homo sapien
```

```
<400> SEQUENCE: 8
ggtcgccccg acgttt                                              16

<210> SEQ ID NO 9
<211> LENGTH: 25
<212> TYPE: DNA
<213> ORGANISM: Homo sapien

<400> SEQUENCE: 9
ccacgtggaa atcaacggga tcagc                                    25

<210> SEQ ID NO 10
<211> LENGTH: 20
<212> TYPE: DNA
<213> ORGANISM: Homo sapien

<400> SEQUENCE: 10
tgcggtgtcc aacacagatc                                          20

<210> SEQ ID NO 11
<211> LENGTH: 22
<212> TYPE: DNA
<213> ORGANISM: Homo sapien

<400> SEQUENCE: 11
gcttcctcag tctgctcact ca                                       22

<210> SEQ ID NO 12
<211> LENGTH: 31
<212> TYPE: DNA
<213> ORGANISM: Homo sapien

<400> SEQUENCE: 12
atggatttca agaacctgct agaccacctg g                             31

<210> SEQ ID NO 13
<211> LENGTH: 18
<212> TYPE: DNA
<213> ORGANISM: Homo sapien

<400> SEQUENCE: 13
gtgccaaggg cctgaatg                                            18

<210> SEQ ID NO 14
<211> LENGTH: 21
<212> TYPE: DNA
<213> ORGANISM: Homo sapien

<400> SEQUENCE: 14
cacctaaagg gctgttgcaa a                                        21

<210> SEQ ID NO 15
<211> LENGTH: 24
<212> TYPE: DNA
<213> ORGANISM: Homo sapien

<400> SEQUENCE: 15
cccagctcta agggtgcccg tgaa                                     24

<210> SEQ ID NO 16
<211> LENGTH: 18
<212> TYPE: DNA
```

<213> ORGANISM: Homo sapien

<400> SEQUENCE: 16
ggaggagagg gcggacat                                      18

<210> SEQ ID NO 17
<211> LENGTH: 23
<212> TYPE: DNA
<213> ORGANISM: Homo sapien

<400> SEQUENCE: 17
agaggttatt cctcgtcgtg cat                                23

<210> SEQ ID NO 18
<211> LENGTH: 20
<212> TYPE: DNA
<213> ORGANISM: Homo sapien

<400> SEQUENCE: 18
atgtcccggc tcttggcccg                                    20

<210> SEQ ID NO 19
<211> LENGTH: 19
<212> TYPE: DNA
<213> ORGANISM: Homo sapien

<400> SEQUENCE: 19
tgcaccacca actgcttag                                     19

<210> SEQ ID NO 20
<211> LENGTH: 19
<212> TYPE: DNA
<213> ORGANISM: Homo sapien

<400> SEQUENCE: 20
ggatgcaggg atgatgttc                                     19

<210> SEQ ID NO 21
<211> LENGTH: 23
<212> TYPE: DNA
<213> ORGANISM: Homo sapien

<400> SEQUENCE: 21
cagaagactg tggatggccc ctc                                23

<210> SEQ ID NO 22
<211> LENGTH: 21
<212> TYPE: DNA
<213> ORGANISM: Homo sapien

<400> SEQUENCE: 22
gtccaccttc cagcagatgt g                                  21

<210> SEQ ID NO 23
<211> LENGTH: 21
<212> TYPE: DNA
<213> ORGANISM: Homo sapien

<400> SEQUENCE: 23
cagtccgcct agaagcactt g                                  21

<210> SEQ ID NO 24
<211> LENGTH: 24

```
<212> TYPE: DNA
<213> ORGANISM: Homo sapien

<400> SEQUENCE: 24
caggagtacg atgagtccgg cccc                                            24
```

MEDICINAL USES OF DIHYDROPYRAZOLES

CROSS REFERENCE TO RELATED APPLICATIONS

This application claims priority under Title 35, United States Code 119(e) from Provisional Application Ser. No. 60/288,720, filed May 4, 2001.

TECHNICAL FIELD

This invention is directed to compounds that are useful in methods of treating hypoxia related disorders. The invention is also directed to pharmaceutical compositions comprising the compounds.

BACKGROUND

Ischemic cardiac disease and peripheral vascular disease are major health problems affecting hundreds of millions of people worldwide. Ischemia results when there is a lack of oxygen supply. It is estimated that about half of the deaths that occur in the United States each year alone are caused by ischemic heart disease. This invention relates, in part, to methods for the treatment of such diseases and pharmaceutical compositions in the treatment thereof.

Oxygen is essential for an organism's survival, given its role in essential metabolic processes including oxidative phosphorylation in which $O_2$ serves as electron acceptor during ATP formation. Tissue damage can result from hypoxia, that is, when oxygen supply in tissue is insufficient to meet metabolic demands. Hypoxia can be caused by various medical conditions, including atherosclerosis, chronic illness, trauma, and surgical procedures. Accordingly, hypoxia plays an important role in the pathogenesis of major causes of mortality, including cancer, cerebral and myocardial ischemia, and chronic heart and lung diseases.

Organisms can sense $O_2$ concentration and adaptively respond to hypoxia. These adaptive responses either increase $O_2$ delivery or activate alternative metabolic pathways that do not require $O_2$. There are a number of hypoxia-inducible gene products that participate in these responses. Included, are genes that code for erythropoietin (hereinafter "EPO"), vascular endothelia growth factor (hereinafter "VEGF"), tyrosine hydroxylase, and glycolytic enzymes. See Bunn, H. F & Poyton, R. O., "Oxygen sensing and molecular adaptation to hypoxia", *Physiol. Rev.*, Vol. 76, pp. 839–885 (1996); Semenza, G. L., "Regulation of mammalian $O_2$ homeostasis by hypoxia-inducible factor 1", *Annu. Rev. Cell. Dev. Biol.*, Vol. 15, pp. 551–578 (1999); Shweiki, D., et al., "Induction of vascular endothelial growth factor expression by hypoxia and by glucose deficiency in multi-cell spheroids: implications for tumor angiogenesis", *Proc. Natl. Acad. Sci. U.S.A.*., Vol. 92, pp. 768–772 (1995). The transcriptional regulator hypoxia-inducible factor 1 (hereinafter "HIF-1") is an essential mediator of $O_2$ homeostasis and regulates the transcription rate of many genes including the aforementioned genes. See Wang, G. L., et al., *Biochem. Biophys. Res. Commun.*, Vol. 86, pp. 15–22 (1995). The number of target genes activated by HIF-1 includes genes whose protein products are involved in angiogenesis, energy metabolism, erythropoiesis, cell proliferation and viability, vascular remodeling, and vasomotor responses. Semenza, G. L., "HIF-1: mediator of physiological and pathophysiological responses to hypoxia," *J. Appl. Physiol.* Vol. 88, pp. 1474–1480 (2000); Semenza, G. L., "Hypoxia-inducible factor 1: master regulator of $O_2$ homeostasis," *Genetics & Development*, Vol. 8, pp. 588–594 (1998).

Structurally, HIF-1 is a heterodimer of two subunits, HIF-1α and HIF-1β. The biological activity of HIF-1 is determined by the expression and activity of the HIF-1α subunit. See Jiang, B-H, et al., "Transactivation and inhibitory domains of hypoxia-inducible factor 1α: modulation of transcriptional activity by oxygen tension", *J. Biol. Chem.*, Vol. 272, pp. 19253–60 (1997). The in vivo regulation of HIF-1α biological activity occurs at multiple levels, including mRNA expression, protein expression, nuclear localization, and transactivation. Semenza, *J. Appl. Physiol.*, Vol. 88, page 1476 (2000). Hypoxia, in turn, is known to have at least two independent effects on HIF-1α activity: (1) hypoxia increases the steady-state levels of HIF-1α protein by stabilizing it (i.e., decreasing its degradation); and (2) hypoxia increases the specific transcriptional activity of the protein (i.e., independent of the protein concentration). Jiang, B. H., et al., "Dimerization, DNA binding, and transactivation properties of hypoxia-inducible factor 1," *J. Biol. Chem.*, Vol. 271, pp. 17771–78 (1996). Given HIF-1's role in hypoxia, treatments utilizing HIF-1 in the treatment of hypoxia-related disorders, have been described. For example, U.S. Pat Nos. 5,882,914; 6,020,462; 6,124,131 and international publication number WO 00/10578.

Although the known number of target genes activated by HIF-1 continues to increase, the role of HIF-1 in the activation of VEGF gene transcription in hypoxic cells is well established. Semenza, *J. Appl. Physiol.* Vol. 88, page 1477 (2000). VEGF itself mediates a number of responses including vasodilation, vascular permeability, and endothelial cell migration and proliferation through receptors that are restricted to vascular endothelium and certain hematopoietic cells. The combined effects of VEGF are important to the promotion of an angiogenic response. The restricted localization of VEGF receptors provides a level of specificity that makes VEGF an important target for angiogenic therapy. For example, the promotion of blood vessel growth has been demonstrated in animal models of coronary and limb ischemia. See Pearlman, J. D., et al., "Magnetic resonance mapping demonstrates benefits of VEGF-induced myocardial angiogenesis", *Nat. Med.* Vol. 1, pp. 1085–1089 (1995); Takeshita, S., et al., "Therapeutic angiogenesis. A single intraarterial bolus of vascular endothelial growth factor augments revascularization in a rabbit ischemic hind limb model", *J. Clin. Invest.*, Vol. 93, pp. 662–670 (1994). There are several clinical trials in progress to assess the efficacy of both exogenously administered VEGF protein as well as expression vectors for the VEGF gene. See Hendel, R. C., et al., "Effect of intracoronary recombinant human vascular endothelial growth factor on myocardial perfusion—Evidence for a dose-dependent effect", *Circulation*, Vol. 101(2), pp. 118–121 (2000); Schwarz, et al., "Evaluation of the effects of intramyocardial injection of DNA expressing vascular endothelial growth factor in a myocardial infarction model in the rat—Angiogenesis and angioma formation", *J. Amer. Coll. Cardiol.*, Vol. 35(5), pp. 1323–1330 (2000).

Another approach to utilizing the effects of VEGF in proangiogenic therapy is to stimulate its production from the tissues needing new vessels. Secretion of VEGF appears to be dependent on its rate of biosynthesis since the intracellular storage of VEGF protein has not been demonstrated. The biosynthesis of VEGF is primarily controlled by regulating the amount of VEGF mRNA. See Shweiki, D., et al, "Vascular endothelial growth factor induced by hypoxia may mediate hypoxia-initiated angiogenesis", *Nature*, Vol. 359, pp. 843–845 (1992). In turn, the amount of mRNA is controlled by activation of transcription through regulatory elements located in the 5' promoter sequence of the VEGF gene as well as by less characterized mechanisms that stabilize VEGF mRNA. See Levy, A. P., et al., "Transcriptional regulation of the rat vascular endothelial growth factor gene by hypoxia", *Drug Discov. Today*, Vol. 270, pp. 13333–13340 (1995); Ikeda, E., et al., "Hypoxia-induced transcriptional activation and increased mRNA stability of vascular endothelial growth factor in C6 glioma cells", *J. Biol. Chem.*, Vol. 270, pp. 19761–19766 (1995); Levy, A. P., et al., "Post-transcriptional regulation of vascular endothelial growth factor by hypoxia", *Drug Discov. Today*, Vol. 271, pp. 2746–2753 (1996).

Various treatments using VEGF have been suggested (e.g., U.S. Pat. No. 5,073,492 issued Dec. 17, 1991; U.S. Pat. No. 5,194,596 issued Mar. 16, 1993; and U.S. Pat. No. 5,219,739 issued Jun. 15, 1993) for ameliorating conditions such as myocardial infarction, diabetic ulcers, and surgical wounds. In particular, several small molecules have been described which mimic the hypoxic induction of VEGF by activating HIF-1α. However, many of these molecules, such as cobaltous chloride or deferoxamine cannot be considered candidate drug-like molecules because of unfavorable pharmacokinetic characteristics. Still other molecules, such as mersalyl, cannot be considered because of their reactivity. See Agani, F. & Semenza, G. L., "Mersalyl is a novel inducer of vascular endothelial growth factor gene expression and hypoxia-inducible factor 1 activity", *Mol. Pharmacol.*, Vol. 54, pp. 749–754 (1998). Although several growth factors, such as platelet derived growth factor-BB, transforming growth factor β1, and hepatocyte growth factor, have also been shown to induce VEGF, their effects may be limited to certain tissue types and transformed cell lines and therefore are probably not mediated through HIF-1α. See Brogi, E., et al., "Indirect angiogenic effect of scatter factor/hepatocyte growth factor via induction of vascular endothelial growth factor; the case for paracrine amplification of angiogenesis", *Circulation*, Vol. 90, pp. 649–652 (1994); Van, B. E., et al., "Potentiated angiogenic effect of scatter factor/hepatocyte growth factor via induction of vascular endothelial growth factor: the case for paracrine amplification of angiogenesis", *Circulation*, Vol. 90, pp. 381–390 (1998). Therefore, there exists a continuing need to identify classes of compounds that induce VEGF at the transcriptional level to increase vascularization of afflicted tissue for the treatment of the aforementioned disorders.

HIF-1 is a transcription factor that also regulates the hypoxia-inducible EPO gene. HIF-1 binding is required for EPO transcriptional activation in response to hypoxia. Semenza, G. L.,"Regulation of erythropoietin production: New insights into molecular mechanisms of oxygen homeostasis", *Hematol. Oncol. Clin. North Am.*, Vol. 8, pp. 863–884 (1994). In particular, HIF-1α binds to the 3' hypoxia-response element of the EPO gene which results in the marked enhancement of EPO transcription. Semenza, G. L., et al. "Transcriptional regulation of genes encoding glycolytic enzymes by hypoxia-inducible factor 1", *J. Biol. Chem.*, Vol. 269, pp. 23757–63 (1994). EPO, in turn, is essential for maintenance of red blood cells by controlling the proliferation and differentiation of erythroid progenitor cells into red blood cells. Krantz, S. B., "Erythropoietin," *Blood*, Vol. 77, pp 419–434 (1991). During fetal development, the liver serves as the primary source of EPO. Shortly before birth, production of EPO in the liver decreases and the kidney becomes the primary source of EPO. However, in adults other organs such as the liver and brain produce small but significant amounts of EPO. A erythropoietin deficiency is associated with anemia. In humans, the most prevalent form of anemia is associated with kidney failure.

Compounds have been described that enhance the biosynthesis of EPO such as those described in U.S. Pat. No. 5,985,913 issued Nov. 16, 1999. Another approach is using injectable recombinant EPO, which is currently the therapy of choice for the treatment of anemia due to chronic renal failure. EPO has been described in the treatment of anemia: associated with chemotherapy; that occurs as a consequence of AIDS; and due to prematurity and autologous blood donation. EPO has even been suggested as a general use agent in pre-operative elective surgery. However, its extensive use could be limited by high production costs and lack of oral bioavailability. See Qureshi, S. A., et al., "Mimicry of erythropoietin by a nonpeptide molecule", *PNAS*, Vol. 96(21) pp. 12156–61 (1999). Therefore, there exists a continuing need for the development of classes of molecules that increase endogenous EPO at the transcriptional level for the treatment of the aforementioned disorders.

Thus, it would be advantageous to identify a class of compounds that are effective in treating hypoxia related disorders.

SUMMARY OF INVENTION

The present invention identifies and provides compounds that are effective in treating hypoxia related disorders. While not intending to be limited by theory, it is believed that the compounds herein function by increasing endogenous EPO and vascularization of tissue in a subject in need of such treatment. Given the ability of these compounds to induce EPO, these molecules can be important for the treatment and prophylaxis of anemia associated with kidney disease, as a combination therapy with chemotherapy, in preparation for autologous blood donation, and other cases of chronic anemia. Furthermore, given the ability of these compounds to increase vascularization in tissue, these molecules can be important for the treatment of ischemic heart disease, for treating peripheral vascular disease, and for the enhancement of wound healing. Other uses of these compounds include: neuroprotection in cerebral ischemic conditions; and reducing or preventing hypoxia related disorders of cerebral, coronary, or peripheral circulation.

In particular, the present invention relates to compounds having a structure according to Formula (I):

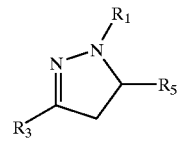

Formula (I)

wherein
(a) $R_1$ is selected from the group consisting of alkyl, alkene, alkyne, cycloalkyl, heteroalkyl, aryl, heteroaryl, and heterocycloalkyl.
(b) $R_3$ is selected from the group consisting of aryl, heteroaryl, and heterocycloalkyl;
(c) $R_5$ is selected from the group consisting of aryl and heteroaryl.

This invention also includes optical isomers, diastereomers and enantiomers of the formula above, and pharmaceutically acceptable salts, biohydrolyzable amides, esters, and imides thereof.

The compounds of Formula (I) are useful in the treatment of hypoxia related disorders. In particular, the invention provides a method of increasing vascularization of tissue in a subject, and a method for increasing EPO in a subject, by administering the compounds of Formula (I). Accordingly, the invention further provides pharmaceutical compositions comprising these compounds.

DETAILED DESCRIPTION OF THE INVENTION

I. Terms and Definitions:

All percentages, ratios and proportions herein are by weight, unless otherwise specified.

All documents described herein are hereby incorporated by reference.

When describing the compounds involved in the subject invention, the following terms have the following meanings unless otherwise specified.

"Acyl" or "carbonyl" is a radical formed by removal of the hydroxy from a carboxylic acid (i.e., R—C(=O)—). Preferred acyl groups include (for example) acetyl, formyl, and propionyl.

"Alkyl" is a saturated hydrocarbon chain having 1 to 15 carbon atoms, preferably 1 to 10, more preferably 1 to 4 carbon atoms. "Alkene" is a hydrocarbon chain having at least one (preferably only one) carbon-carbon double bond and having 2 to 15 carbon atoms, preferably 2 to 10, more preferably 2 to 4 carbon atoms. "Alkyne" is a hydrocarbon chain having at least one (preferably only one) carbon-carbon triple bond and having 2 to 15 carbon atoms, preferably 2 to 10, more preferably 2 to 4 carbon atoms. Alkyl, alkene and alkyne chains (referred to collectively as "hydrocarbon chains") may be straight or branched and may be unsubstituted or substituted. Preferred branched alkyl, alkene and alkyne chains have one or two branches, preferably one branch. Preferred chains are alkyl. Alkyl, alkene and alkyne hydrocarbon chains each may be unsubstituted or substituted with from 1 to 4 substituents; when substituted, preferred chains are mono-, di-, or tri-substituted. Alkyl, alkene and alkyne hydrocarbon chains each may be substituted with halo, hydroxy, aryloxy (e.g., phenoxy), heteroaryloxy, acyloxy (e.g., acetoxy), carboxy, aryl (e.g., phenyl), heteroaryl, cycloalkyl, heterocycloalkyl, spirocycle, amino, amido, acylamino, keto, thioketo, cyano, or any combination thereof. Preferred hydrocarbon groups include methyl, ethyl, propyl, isopropyl, butyl, vinyl, allyl, butenyl, and exomethylenyl.

Also, as referred to herein, a "lower" alkyl, alkene or alkyne moiety (e.g., "lower alkyl") is a chain comprised of 1 to 6, preferably from 1 to 4, carbon atoms in the case of alkyl and 2 to 6, preferably 2 to 4, carbon atoms in the case of alkene and alkyne.

"Alkoxy" is an oxygen radical having a hydrocarbon chain substituent, where the hydrocarbon chain is an alkyl or alkenyl (i.e., —O-alkyl or —O-alkenyl). Preferred alkoxy groups include (for example) methoxy, ethoxy, propoxy and allyloxy.

"Aryl" is an aromatic hydrocarbon ring. Aryl rings are monocyclic or fused bicyclic ring systems. Monocyclic aryl rings contain from 5 to about 9 atoms, preferably from 5 to 7 atoms, most preferably from 5 to 6 atoms, especially 6 carbon atoms in the ring. Six carbon atom ring membered monocyclic aryl rings are also referred to as phenyl rings. Bicyclic aryl rings contain from 8 to 17 carbon atoms, preferably 9 to 12 carbon atoms, in the ring. Bicyclic aryl rings include ring systems wherein one ring is aryl and the other ring is aryl, cycloalkyl, or heterocycloakyl. Preferred bicyclic aryl rings comprise 5-, 6- or 7-membered rings fused to 5-, 6-, or 7-membered rings. Aryl rings may be unsubstituted or substituted with from 1 to 4 substituents on the ring. Aryl may be substituted with halo, cyano, nitro, hydroxy, carboxy, amino, acylamino, alkyl, heteroalkyl, haloalkyl, phenyl, aryloxy, alkoxy, heteroalkyloxy, carbamyl, haloalkyl, methylenedioxy, heteroaryloxy, or any combination thereof. Preferred aryl rings include naphthyl, tolyl, xylyl, and phenyl. The most preferred aryl ring radical is phenyl.

"Aryloxy" is an oxygen radical having an aryl substituent (i.e., —O-aryl). Preferred aryloxy groups include (for example) phenoxy, napthyloxy, methoxyphenoxy, and methylenedioxyphenoxy.

"Cycloalkyl" is a saturated or unsaturated hydrocarbon ring. Cycloalkyl rings are not aromatic. Cycloalkyl rings are monocyclic, or are fused, spiro, or bridged bicyclic ring systems. Monocyclic cycloalkyl rings contain from about 3 to about 9 carbon atoms, preferably from 3 to 7 carbon atoms, in the ring. Bicyclic cycloalkyl rings contain from 7 to 17 carbon atoms, preferably from 7 to 12 carbon atoms, in the ring. Preferred bicyclic cycloalkyl rings comprise 4-, 5-, 6- or 7-membered rings fused to 5-, 6-, or 7-membered rings. Cycloalkyl rings may be unsubstituted or substituted with from 1 to 4 substituents on the ring. Cycloalkyl may be substituted with halo, cyano, alkyl, heteroalkyl, haloalkyl, phenyl, keto, hydroxy, carboxy, amino, acylamino, aryloxy, heteroaryloxy, or any combination thereof. Preferred cycloalkyl rings include cyclopropyl, cyclopentyl, and cyclohexyl.

"Halo" or "halogen" is fluoro, chloro, bromo or iodo. Preferred halo are fluoro, chloro and bromo; more preferred typically are chloro and fluoro, especially fluoro.

"Haloalkyl" is a straight, branched, or cyclic hydrocarbon substituted with one or more halo substituents. Preferred are $C_1$–$C_{12}$ haloalkyls; more preferred are $C_1$–$C_6$ haloalkyls; still more preferred still are $C_1$–$C_3$ haloalkyls. Preferred halo substituents are fluoro and chloro. The most preferred haloalkyl is trifluoromethyl.

"Heteroatom" is a nitrogen, sulfur, or oxygen atom. Groups containing more than one heteroatom may contain different heteroatoms.

"Heteroalkyl" is a saturated or unsaturated chain containing carbon and at least one heteroatom, wherein no two heteroatoms are adjacent. Heteroalkyl chains contain from 2 to 15 member atoms (carbon and heteroatoms) in the chain, preferably 2 to 10, more preferably 2 to 5. For example, alkoxy (i.e., —O-alkyl or —O-heteroalkyl) radicals are included in heteroalkyl. Heteroalkyl chains may be straight or branched. Preferred branched heteroalkyl have one or two branches, preferably one branch. Preferred heteroalkyl are saturated. Unsaturated heteroalkyl have one or more carbon-carbon double bonds and/or one or more carbon-carbon triple bonds. Preferred unsaturated heteroalkyls have one or two double bonds or one triple bond, more preferably one double bond. Heteroalkyl chains may be unsubstituted or substituted with from 1 to 4 substituents. Preferred substituted heteroalkyl are mono-, di-, or tri-substituted. Heteroalkyl may be substituted with lower alkyl, haloalkyl, halo, hydroxy, aryloxy, heteroaryloxy, acyloxy, carboxy, monocyclic aryl, heteroaryl, cycloalkyl, heterocycloalkyl, spirocycle, amino, acylamino, amido, keto, thioketo, cyano, or any combination thereof.

"Heteroaryl" is an aromatic ring containing carbon atoms and from 1 to about 6 heteroatoms in the ring. Heteroaryl rings are monocyclic or fused bicyclic ring systems. Monocyclic heteroaryl rings contain from about 5 to about 9 member atoms (carbon and heteroatoms), preferably 5 or 6 member atoms, in the ring. Bicyclic heteroaryl rings contain from 8 to 17 member atoms, preferably 8 to 12 member atoms, in the ring. Bicyclic heteroaryl rings include ring systems wherein one ring is heteroaryl and the other ring is aryl, heteroaryl, cycloalkyl, or heterocycloalkyl. Preferred bicyclic heteroaryl ring systems comprise 5-, 6- or 7-membered rings fused to 5-, 6-, or 7-membered rings. Heteroaryl rings may be unsubstituted or substituted with from 1 to 4 substituents on the ring. Heteroaryl may be substituted with halo, cyano, nitro, hydroxy, carboxy, amino, acylamino, alkyl, heteroalkyl, haloalkyl, phenyl, alkoxy, aryloxy, heteroaryloxy, or any combination thereof. Preferred heteroaryl rings include, but are not limited to, the following:

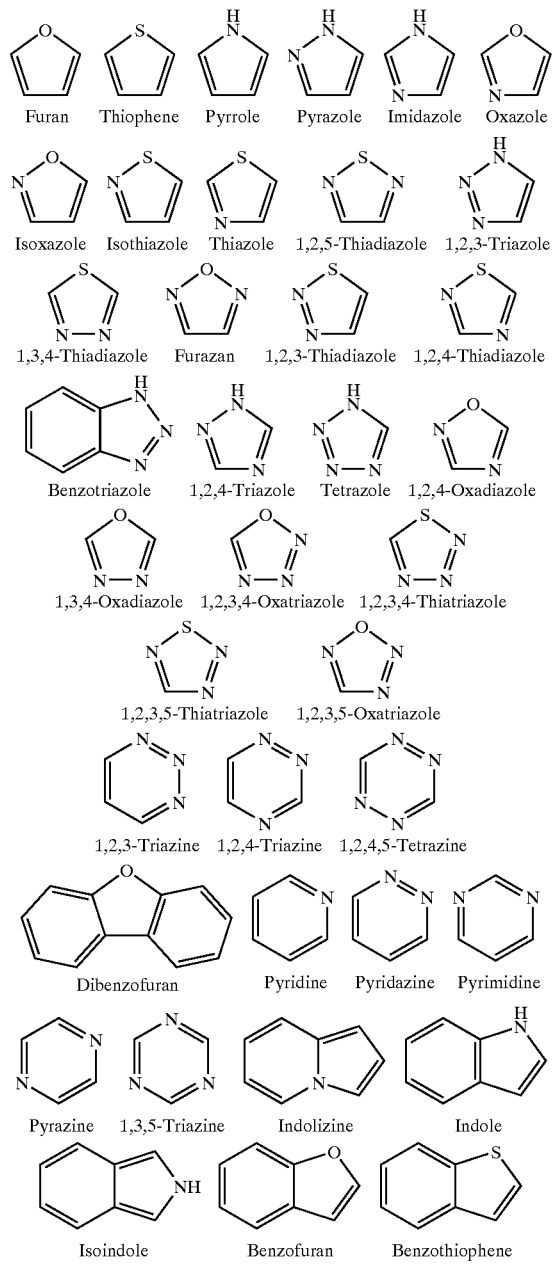

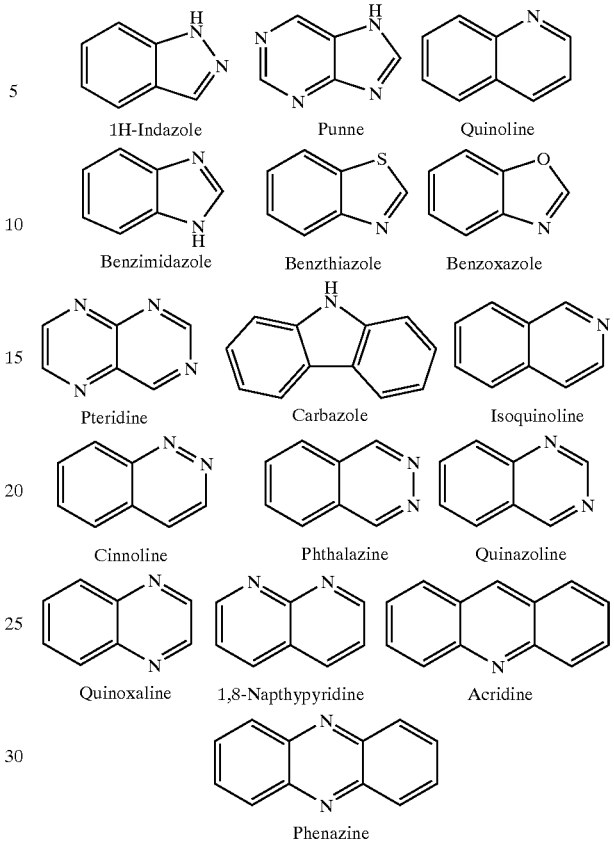

"Heteroaryloxy" is an oxygen radical having a heteroaryl substituent (i.e., —O-heteroaryl). Preferred heteroaryloxy groups include (for example) pyridyloxy, furanyloxy, (thiophene)oxy, (oxazole)oxy, (thiazole)oxy, (isoxazole)oxy, pyrmidinyloxy, pyrazinyloxy, and benzothiazolyloxy.

"Heterocycloalkyl" is a saturated or unsaturated ring containing carbon atoms and from 1 to about 4 (preferably 1 to 3) heteroatoms in the ring. Heterocycloalkyl rings are not aromatic. Heterocycloalkyl rings are monocyclic, or are fused, bridged, or spiro bicyclic ring systems. Monocyclic heterocycloalkyl rings contain from about 3 to about 9 member atoms (carbon and heteroatoms), preferably from 5 to 7 member atoms, in the ring. Bicyclic heterocycloalkyl rings contain from 7 to 17 member atoms, preferably 7 to 12 member atoms, in the ring. Bicyclic heterocycloalkyl rings contain from about 7 to about 17 ring atoms, preferably from 7 to 12 ring atoms. Bicyclic heterocycloalkyl rings may be fused, Spiro, or bridged ring systems. Preferred bicyclic heterocycloalkyl rings comprise 5-, 6- or 7-membered rings fused to 5-, 6-, or 7-membered rings. Heterocycloalkyl rings may be unsubstituted or substituted with from 1 to 4 substituents on the ring. Heterocycloalkyl may be substituted with halo, cyano, hydroxy, carboxy, keto, thioketo, amino, acylamino, acyl, amido, alkyl, heteroalkyl, haloalkyl, phenyl, alkoxy, aryloxy or any combination thereof. Preferred substituents on heterocycloalkyl include halo and haloalkyl. Preferred heterocycloalkyl rings include, but are not limited to, the following:

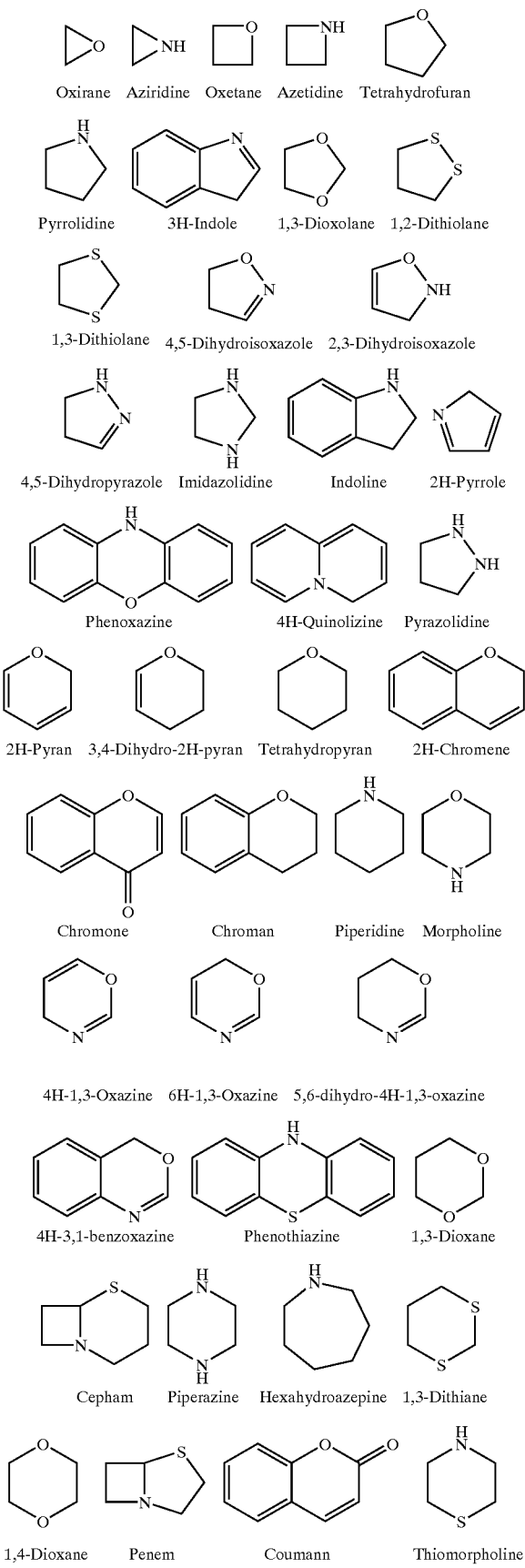

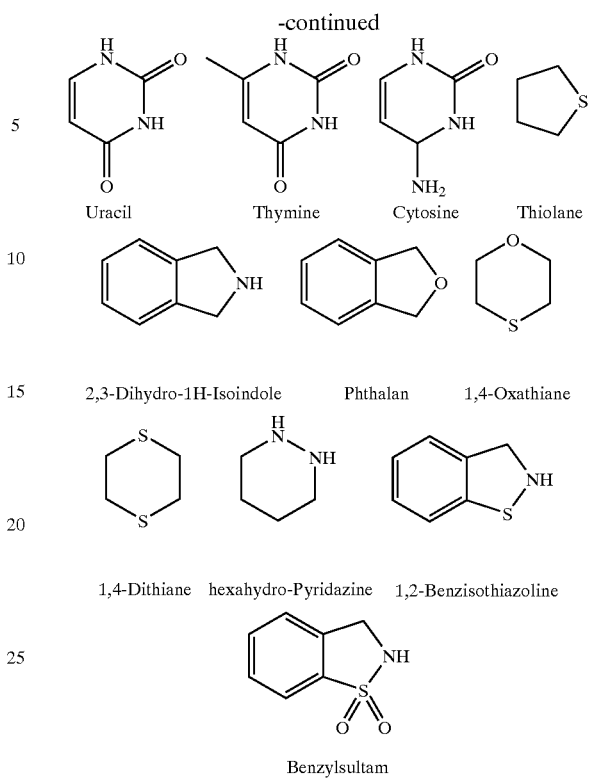

"Spirocycle" is an alkyl or heteroalkyl diradical substituent of alkyl or heteroalkyl wherein said diradical substituent is attached geminally and wherein said diradical substituent forms a ring, said ring containing 4 to 8 member atoms (carbon or heteroatom), preferably 5 or 6 member atoms.

A "pharmaceutically-acceptable salt" is a cationic salt formed at any acidic (e.g., hydroxamic or carboxylic acid) group, or an anionic salt formed at any basic (e.g., amino) group. Many such salts are known in the art, as described in World Patent Publication 87/05297, Johnston, et al., published Sep. 11, 1987, incorporated by reference herein. Preferred cationic salts include the alkali metal salts (such as sodium and potassium), and alkaline earth metal salts (such as magnesium and calcium) and organic salts. Preferred anionic salts include the halides (such as chloride salts), sulfonates, carboxylates, phosphates, and the like.

Such salts are well understood by the skilled artisan, and the skilled artisan is able to prepare any number of salts given the knowledge in the art. Furthermore, it is recognized that the skilled artisan may prefer one salt over another for reasons of solubility, stability, formulation ease and the like. Determination and optimization of such salts is within the purview of the skilled artisan's practice.

A "biohydrolyzable amide" is an amide of a hydroxamic acid-containing compound of Formula (I) that does not interfere with the vascularizing or EPO increasing activity of these compounds, or that is readily converted in vivo by an animal, preferably a mammal, more preferably a human subject, to yield an active compound of Formula I. Examples of such amide derivatives are alkoxyamides, where the hydroxyl hydrogen of the hydroxamic acid of Formula (I) is replaced by an alkyl moiety, and acyloxyamides, where the hydroxyl hydrogen is replaced by an acyl moiety (i.e., R—C(=O)—).

A "biohydrolyzable hydroxy imide" is an imide of a hydroxamic acid-containing compound of Formula (I) that does not interfere with the vascularizing or EPO increasing activity of these compounds, or that is readily converted in vivo by an animal, preferably a mammal, more preferably a human subject to yield an active compound of Formula (I). Examples of such imide derivatives are those where the amino hydrogen of the hydroxamic acid of Formula (I) is replaced by an acyl moiety (i.e., R—C(=O)—).

A "biohydrolyzable ester" is an ester of a hydroxy-containing compound of Formula (I) that does not interfere with the vascularizing or EPO increasing activity of these compounds or that is readily converted in vivo by an animal to yield an active compound of Formula (I). Such esters include lower alkyl esters, lower acyloxy-alkyl esters (such as acetoxymethyl, acetoxyethyl, aminocarbonyloxymethyl, pivaloyloxymethyl and pivaloyloxyethyl esters), lactonyl esters (such as phthalidyl and thiophthalidyl esters), lower alkoxyacyloxyalkyl esters (such as methoxycarbonyloxymethyl, ethoxycarbonyloxyethyl and isopropoxycarbonyloxyethyl esters), alkoxyalkyl esters, choline esters and alkyl acylamino alkyl esters (such as acetamidomethyl esters).

The terms "optical isomer", "stereoisomer", and "diastereomer" have the standard art recognized meanings (see, e.g., Hawley's Condensed Chemical Dictionary, 11th Ed.). The illustration of specific protected forms and other derivatives of the compounds of the instant invention is not intended to be limiting. The application of other useful protecting groups, salt forms, etc. is within the ability of the skilled artisan.

II. Compounds:

The invention relates to the method of using the compounds of Formula (I):

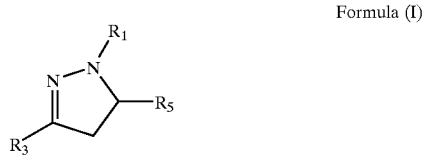

Formula (I)

where $R_1$, $R_3$, and $R_5$ have the meanings described above. The following provides a description of particularly preferred moieties, but is not intended to limit the scope of the claims.

$R_1$ is selected from the group consisting of: alkyl, alkene, alkyne, cycloalkyl, heteroalkyl, aryl, heteroaryl, and heterocycloalkyl. When $R_1$ is a heteroaryl, $R_1$ in one mode has a heteroatom in the 2-position. $R_1$ may be 2-pyridine.

$R_3$ is selected from the group consisting of aryl, heteroaryl, and heterocycloalkyl. In one mode, $R_3$ is aryl or heteroaryl. In another mode $R_3$ is aryl substituted in the 2-position with at least hydroxy. In still another mode, $R_3$ is further selected from the group consisting of 2-pyridyl, phenyl, 2-hydroxyphenyl, 3-naphthyl.

$R_5$ is selected from the group consisting of aryl and heteroaryl. In one mode $R_5$ is further selected from the group consisting of phenyl, and m-chlorophenyl.

III. Compound Preparation:

The compounds of the invention can be prepared using a variety of procedures. The starting materials used in preparing the compounds of the invention are known, made by known methods, or are commercially available. A particularly preferred synthesis is described in the following general reaction scheme. Specific examples for making the compounds of the present invention are set forth in Section VII, below.

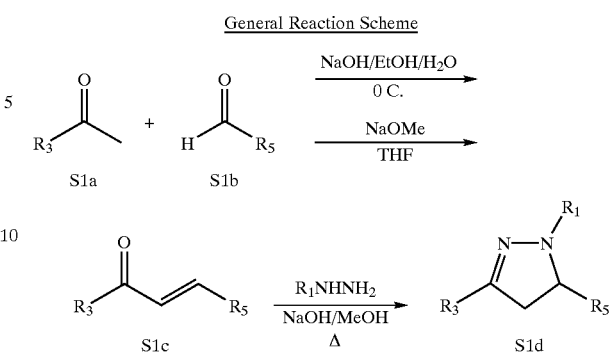

General Reaction Scheme

In the general reaction scheme, $R_1$, $R_3$, and $R_5$ are defined above. S1a and S1b starting materials are generally commercially available (such as from Aldrich, TCI, or Lancaster). Some di-aromatic enones or chalcones are generally commercially available (such as from Aldrich, TCI, or Pfaltz and Bauer). Hydrazine derivatives are generally commercially available (such as from Aldrich, Pfatz & Bauer, or Lancaster). Compounds described by S1d, that is Formula (I) can be made by methods known to one of ordinary skill in the art, as described by the following and in cited references.

In the above general reaction scheme, the aryl or heteroaryl ketone depicted as S1a is reacted with an aryl or heteroaryl aldehyde depicted as S1b in a solvent that will allow the formation of the enone to take place. Preferred solvents include small (C1–C4) aliphatic alcohols that may or may not be wet with water, or a higher boiling ether such as tetrahydrofuran. The more preferred solvent is methanol or ethanol. The most preferred solvent is ethanol. Subsequently, a base is added to the reaction. Preferred bases include but are not limited to methoxides or hydroxides. A preferred base is sodium hydroxide. The reaction is allowed to proceed at a temperature preferably between about −50° C. and about 75° C., more preferably between about −20° C. and about 45° C., and most preferred between about 0° C. and about 25° C. The reaction time is preferably between about 1 and about 24 hours, more preferably between about 4 and about 20 hours, and the most preferred between about 8 and about 16 hours. Kohler, E. P. & H. M. Chadwell, Org. Synth., Coll. Vol. 1, $2^{nd}$ ed., p. 78; and Hollinshead, S. P., Tetrahedron Letters, Vol. 37, pp. 9157–9160 (1996).

The resulting one depicted as S1c is isolated by methods known to those of ordinary skill in the art. Such methods include, but are not limited to, extraction, solvent evaporation, precipitation and filtration, or by flash chromatography on silica gel (Merck, 230–400 mesh) using a mixture of solvents, preferably hexanes and ethyl acetate, or dichloromethane and methanol, the most preferred being dichloromethane and methanol. Most preferable methods of isolation are precipitation and filtration, or extraction into organic media, followed by flash column chromatography.

The di-aryl/heteroaryl enone S1c is easily reacted with a variety of hydrazines, either free base, or the mono- or di-hydrochloride salt as depicted, for example, in Powers, D. G., et al., Tetrahedron, Vol. 54, pp. 4085–4096 (1998). The most preferred hydrazine is free base. The enone intermediate S1c is placed in a solvent suitable for the reaction in flasks open to atmospheric pressure, or in tubes that are sealed during the reaction while heating takes place, such as on a Quest™ 210 Organic Synthesizer (Argonaut Technologies) as to allow pressure to build in the system. Preferred solvents include small aliphatic alcohols (C1–C4)

such as methanol, ethanol, or isopropanol, or dimethyl sulfoxide, tetrahydrofuran, or dimethylformamide. More preferred solvents are small aliphatic alcohols or dimethylsulfoxide. The most preferred solvent is ethanol. An amount of base is added dependent on the species of hydrazine, free base, mono or dihydrochloride salt. A preferred base is sodium hydroxide.

Addition of hydrazine is followed by heating the reaction. The cyclization is carried out at a temperature between about 0° C. and about 140° C. The preferred temperature range is between 30° C. and 110° C. The most preferred range is between 55° C. and 85° C. The preferred time for reaction completion is about 1 to about 15 hours. The more preferred reaction time is between about 3 and about 12 hours. The most preferred reaction time is between about 5 and about 10 hours.

The 1,3,5-substituted dihydropyrazole noted as S1d is isolated by methods known to one of ordinary skill in the art. Such methods include, but are not limited to, extraction, solvent evaporation, high pressure liquid chromatography (Gilson HPLC, 5%–95% methanol in water, 9 minute gradient, 210 nm), precipitation followed by filtration, or crystallization followed by filtration.

These steps may be varied to increase yield of desired product. The skilled artisan will recognize the judicious choice of reactants, solvents, and temperatures is an important considerations in any successful synthesis. Determination of optimal conditions, etc., is routine. Thus, the skilled artisan can make a variety of compounds using the guidance of the scheme above.

It is recognized that the skilled artisan in the art of organic chemistry can readily carry out standard manipulations of organic compounds without further direction; that is, it is well within the scope and practice of the skilled artisan to carry out such manipulations. These include, but are not limited to, reduction of carbonyl compounds to their corresponding alcohols, oxidations of hydroxyls and the like, acylations, aromatic substitutions, both electrophilic and nucleophilic, etherifications, esterification and saponification and the like. Examples of these manipulations are discussed in standard texts such as March, *Advanced Organic Chemistry* (Wiley), Carey and Sundberg, *Advanced Organic Chemistry* (Vol. 2) and other art that the skilled artisan is aware of.

The skilled artisan will also readily appreciate that certain reactions are best carried out when another potentially reactive functionality on the molecule is masked or protected, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene, *Protecting Groups in Organic Synthesis.*

The compounds of the invention may have one or more chiral centers. As a result, one may selectively prepare one optical isomer, including diastereomer and enantiomer, over another, for example by chiral starting materials, catalysts or solvents, or may prepare both stereoisomers or both optical isomers, including diastereomers and enantiomers, at once (a racemic mixture). Since the compounds of the invention may exist as racemic mixtures, mixtures of optical isomers, including diastereomers and enantiomers, or stereoisomers may be separated using known methods, such as chiral salts, chiral chromatography and the like.

In addition, it is recognized that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantiomers, or stereoisomers substantially free of the other are disclosed and claimed as well.

IV. Methods of use:

The compounds of present invention increase the biological activity of HIF-1, thereby increasing the transcription of HIF-1 target genes. Without wishing to be bound by theory, the compounds of the present invention are believed to increase the biological activity of HIF-1 by one or more of the following mechanisms: i) increasing the mRNA expression of HIF-1; ii) increasing the expression of the protein HIF-1; iii) enhancing the nuclear localization of HIF-1; and iv) enhancing the transactivation of HIF-1. Semenza, *J. Appl. Physiol.*, Vol. 88, page 1476 (2000). The increased biological activity HIF-1, in turn, leads to the increased expression of a number of HIF-1 target genes. A non-exhaustive list of HIF-1 target genes include: adenylate kinase 3, $\alpha_{1B}$-adrenergic receptor, adrenomedullin, aldolase A, aldolase C, endothelin-1, enolase 1, EPO, glucose transporter 1, glucose transporter 3, glyceraldehyde phosphate dehydrogenase, heme oxygenase-1, hexokinase 1, hexokinase 2, insulin-like growth factor II, IGF binding protein 1, IGF factor binding protein 3, lactate dehydrogenase A, nitric oxide synthase 2, p21, p35srj, phosphofructokinase L, phosphoglycerate kinase 1, pyruvate kinase M, transferrin, transferrin receptor, VEGF, VEGF receptor FLT-1. Semenza, *J. Appl. Physiol.*, Vol. 88, pp. 1474–1480 (2000).

By increasing the transcription of these HIF-1 target genes, the compounds of the present invention provide a method of increasing the vascularization of tissue in a subject. As used herein, "vascularization of tissue" means a pro-angiogenic response whereby blood vessels or other vessels or ducts develop at or around the afflicted tissue. The afflicted tissue need not be hypoxic or ischemic per se, but rather the compounds Formula (I) mimic the body's pro-angiogenic response to hypoxia. A non-limiting example of "vascularization" includes capillary proliferation in a non-healing wound or along the border of ischemic tissue. Thus, these compounds enhance the ability of the body to revascularize damaged tissues or increase vasculature (e.g. to prevent hypoxic damage). Non-limiting examples of "tissue" include: cardiac tissue, such as myocardium and cardiac ventricles; skeletal muscle; neurological tissue, such as from the cerebellum; internal organs, such as the stomach, intestine, pancreas, liver, spleen, and lung; and distal appendages such as fingers and toes.

The subject population that would benefit from treatment with these compounds is large and includes any subjects requiring pro-angiogenic treatment or recovery from endothelial cell damage or loss. Examples would be subjects with hypoxia/ischemia-related tissue damage or coronary, cerebral, or peripheral arterial disease. Further examples include those subjects with atherosclerosis, those with diabetic pathology including chronic skin lesions, any subject with bone fractures or wounds that do not heal readily, subjects recovering from surgeries that require rapid revascularization of affected areas or where endothelium is damaged (e.g., vascular graft surgery, balloon angioplasty) or many surgically-related conditions (that is, conditions that often lead to surgery and are caused by surgery) such as oral ulcers, peptic ulcers, Crohn's disease, skin grafts, and wound healing, or those with conditions such as frostbite, gangrene, erectile dysfunction, hair loss, or poor circulation. Still further examples include those subjects presenting with transient ischemic attacks or angina. The compounds of the present invention may also be involved in extra vascularization, where surrounding tissue needs to be broken down to allow new blood vessels such as in angiofibroma and hemangioma.

Vascularization of tissue can be measured by any person skilled in the art using standard techniques. Non-limiting examples of measuring vascularization in a subject include: SPECT (single photon emission computed tomography); PET (positron emission tomography); MRI (magnetic resonance imaging) and combinations thereof, by measuring blood flow to the tissue before and after treatment. These and other techniques are discussed in Simons, et al., "Clinical trials in coronary angiogenesis", *Circulation*, Vol. 102, pp. 73–86 (2000) incorporated herein by reference.

By increasing the transcription of these HIF-1 target genes, the compounds of the present invention also provide a method of increasing EPO in a subject. EPO transcription is subject to physiological regulation at the level of gene transcription in response to hypoxia, a process that can be mimicked by the compounds of the present invention by increasing the biological activity of the transcription factor HIF-1. Thus, these compounds enhance the ability of the body to increase EPO.

The subject population that would benefit from treatment with these compounds is also large and includes any subjects exhibiting an erythropoietin deficiency. As used herein, "erythropoietin deficiency," refers to those conditions in which a subject exhibits either a below normal hematocrit and a below normal level of EPO, or a below normal hematocrit and an average level of EPO, or a normal hematocrit and a below normal EPO. Any person skilled in the art, using standard methods, can measure the hematocrit and EPO levels in blood. A non-limiting example of measuring EPO includes an EPO-ELISA kit from R&D Systems (catalogue # DEP00, Minneapolis, Minn.). Another example of measuring EPO includes a competitive radioimmunoassay as described by Garcia, et al., "Radioimmunoassay of erythropoietin," Blood Cells, Vol. 5, pp. 405–419 (1979) incorporated herein by reference.

Examples of a subject population exhibiting an erythropoietin deficiency include those subjects exhibiting an erythropoietin deficiency associated with anemia. In another example, the erythropoietin deficiency is associated with anemia due to chronic renal failure. Other non-limiting examples of other deficiencies associated with anemia include, but are not limited to, anemia due to: prematurity; autologous blood donation; chronic infection; rheumatoid arthritis; AIDS; AZT-treated HIV-infection; malignancies; stem cell therapy; and anemia associated with: irritable-bowel disease; hypothyroidism; malnutrition; chemotherapy; and bone marrow transplantation.

Though not essential for activity or efficacy, certain diseases, disorders, and unwanted conditions preferably are treated with compounds that act on the afflicted tissues or regions of the body. For example, a compound that displays a higher degree of affinity for the heart would be preferred for treatment of ischemic heart disease by increasing vascularization to the cardiac tissue than other compounds that are less specific.

In addition, certain compounds are more bioavailable to certain tissues that others. Choosing a compound which is more bioavailable to a certain tissue and which acts on the hypoxia-related disorder found in that tissue provides for the specific treatment of the disease, disorder, or unwanted condition. For example, compounds of this invention may vary in their ability to penetrate in neurological tissue. Thus, compounds may be selected for neurological protection from hypoxia (e.g., stroke) by increasing vascularization to the neurological tissue. See, e.g., Bergeron, M., et al., "Role of hypoxia-inducible factor-1 in hypoxia-induced ischemic tolerance in neonatal rat brain," *Ann. Neuro.*, Vol. 48(3), pp. 285–96, (2000); Marti, H. J., et al., "Hypoxia-induced vascular endothelial growth factor expression precedes neovascularization after cerebral ischemia," *Am. J. Pathol.*, Vol. 156(3), pp. 965–76 (2000).

Determination of the specificity of a compound to a particular type of tissue is within the skill of the artisan in that field. For example, if increasing EPO in an adult subject is the therapeutic goal, the ability of compounds of the present invention to increase EPO production in kidney cells can be screened by their ability to increase blood plasma level of EPO via a radioimmunoassay (e.g., DiaSorin).

The compounds of this invention are also useful for prophylactic or acute treatment. They are administered in any way the skilled artisan in the fields of medicine or pharmacology would desire. It is immediately apparent to the skilled artisan that preferred routes of administration would depend upon the disease state being treated and the dosage form chosen. Preferred routes for systemic administration include administration perorally or parenterally.

However, the skilled artisan will readily appreciate the advantage of administering the compounds of the present invention directly to the affected area for many diseases, disorders, or unwanted conditions. For example, given the compounds of the present invention increase vascularization of tissue, it may be advantageous to administer the compounds directly to the area of the tissue in need of vascularization such as in the area affected by surgical trauma (e.g., angioplasty), non-healing wound (e.g., topical to the skin), or for opthalmic and periodontal indications.

V. Compositions:

The compositions of the invention comprise:
(a) a safe and effective amount of a compound of the invention; and
(b) a pharmaceutically-acceptable carrier.

As discussed above, hypoxia plays an important role in the pathogenesis of many diseases and disorders. The compounds of the present invention are useful in therapy with regard to these hypoxia related conditions as well as treating tissue in need of pro-angiogenic therapy and increasing EPO.

The invention compounds can therefore be formulated into pharmaceutical compositions for use in increasing vascularization of tissue and increasing EPO. Standard pharmaceutical formulation techniques are used, such as those disclosed in *Remington's Pharmaceutical Sciences*, Mack Publishing Company, Easton, Pa., latest edition.

A "safe and effective amount" of a Formula (I) compound is an amount that is effective, to increase vascularization and/or increase EPO at the site(s) of activity, in an animal, preferably a mammal, more preferably a human subject, without undue adverse side effects (such as toxicity, irritation, or allergic response), commensurate with a reasonable benefit/risk ratio when used in the manner of this invention. The specific "safe and effective amount" will, obviously, vary with such factors as the particular condition being treated, the physical condition of the patient, the duration of treatment, the nature of concurrent therapy (if any), the specific dosage form to be used, the carrier employed, the solubility of the Formula (I) compound therein, and the dosage regimen desired for the composition.

In addition to the subject compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to an animal, preferably a mammal, more preferably a human. The term "compatible", as used herein, means that the components of the composition are capable of being conmmingled with the subject compound, and with each other, in a manner such that there is no interaction that would substantially reduce the pharmaceutical efficacy of the composition under ordinary use situations. Pharmaceutically-acceptable carriers must, of course, be of sufficiently high purity and sufficiently low toxicity to render them suitable for administration to the animal, preferably a mammal, more preferably a human being treated.

Some examples of substances which can serve as pharmaceutically-acceptable carriers or components thereof are: sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tweens®; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

If the subject compound is to be injected, the preferred pharmaceutically-acceptable carrier is sterile, physiological saline, with a blood-compatible colloidal suspending agent, the pH of which has been adjusted to about 7.4.

In particular, pharmaceutically-acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil. Preferably, the pharmaceutically-acceptable carrier, in compositions for parenteral administration, comprises at least about 90% by weight of the total composition.

The compositions of this invention are preferably provided in unit dosage form. As used herein, a "unit dosage form" is a composition of this invention containing an amount of a Formula (I) compound that is suitable for administration to an animal, preferably a mammal, more preferably a human subject, in a single dose, according to good medical practice. These compositions preferably contain from about 5 mg (milligrams) to about 1000 mg, more preferably from about 10 mg to about 500 mg, more preferably from about 10 mg to about 300 mg, of a Formula (I) compound.

The compositions of this invention may be in any of a variety of forms, suitable, for example, for oral, rectal, topical, nasal, ocular or parenteral administration. Depending upon the particular route of administration desired, a variety of pharmaceutically-acceptable carriers well-known in the art may be used. These include solid or liquid fillers, diluents, hydrotropes, surface-active agents, and encapsulating substances. Optional pharmaceutically-active materials may be included, which do not substantially interfere with the inhibitory activity of the Formula (I) compound. The amount of carrier employed in conjunction with the Formula (I) compound is sufficient to provide a practical quantity of material for administration per unit dose of the Formula (I) compound. Techniques and compositions for making dosage forms useful in the methods of this invention are described in the following references, all incorporated by reference herein: *Modern Pharmaceutics*, Chapters 9 and 10 (Banker & Rhodes, editors, 1979); Lieberman et al., *Pharmaceutical Dosage Forms: Tablets* (1981); and Ansel, *Introduction to Pharmaceutical Dosage Forms* 2d Edition (1976).

Various oral dosage forms can be used, including such solid forms as tablets, capsules, granules and bulk powders. These oral forms comprise a safe and effective amount, usually at least about 5%, and preferably from about 25% to about 50%, of the Formula (I) compound. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, and containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration are well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of the subject invention, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, Avicel® RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit® coatings, waxes and shellac.

Compositions of the subject invention may optionally include other drug actives.

Other compositions useful for attaining systemic delivery of the subject compounds include sublingual, buccal, suppository, and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compositions of this invention can also be administered topically to a subject, e.g., by the direct laying on or spreading of the composition on the epidermal or epithelial tissue of the subject, or transdermally via a "patch". Such compositions include, for example, lotions, creams, solutions, gels and solids. These topical compositions preferably comprise a safe and effective amount, usually at least about 0.1%, and preferably from about 1% to about 5%, of the Formula (I) compound. Suitable carriers for topical administration preferably remain in place on the skin as a continuous film, and resist being removed by perspiration or immersion in water. Generally, the carrier is organic in nature and capable of having dispersed or dissolved therein the Formula (I) compound. The carrier may include pharmaceutically-acceptable emollients, emulsifiers, thickening agents, solvents and the like.

VI. Methods of Administration:

This invention also provides methods of increasing vascularization of tissue and/or increasing EPO in a human or other animal subject, by administering a safe and effective amount of a Formula (I) compound to said subject. The methods of the invention are useful in treating or preventing disorders described above.

Compositions of this invention can be administered topically or systemically. Systemic application includes any method of introducing Formula (I) compound into the tissues of the body, e.g., intra-articular, intrathecal, epidural, intramuscular, transdermal, intravenous, intraperitoneal, subcutaneous, sublingual, rectal, ocular, and oral administration. The Formula (I) compounds of the present invention are preferably administered orally.

The specific dosage of inhibitor to be administered, as well as the duration of treatment, and whether the treatment is topical or systemic, are interdependent. The dosage and treatment regimen will also depend upon such factors as the specific Formula (I) compound used, the treatment indication, the ability of the Formula (I) compound to reach minimum inhibitory concentrations to vascularize affected tissue or to increase EPO to desired level, and the personal attributes of the subject (such as weight), compliance with the treatment regimen, and the presence and severity of any side effects of the treatment.

When determining systemic dosage of a compound of Formula (I) wherein the therapeutic goal is to increase vascularization in tissue, any synergistic interactions of the compound with endogenous events occurring in the injured tissue will be taken into account to avoid undesired effects in non-injured tissues. To the extent (if any) there is synergy between endogenous responses to moderate degrees of hypoxia and the compounds of the present invention, systemic administration can be used to generate a tissue specific response. In this manner, angiogenesis would be stimulated in tissues where it is required and potentially harmful neovascularization (e.g., proliferative retinopathy) in already well-vasularized tissues can be controlled or avoided.

Typically, for a human adult (weighing approximately 70 kilograms), from about 5 mg to about 3000 mg, more preferably from about 5 mg to about 1000 mg, more preferably from about 10 mg to about 100 mg, of Formula (I) compound are administered per day for systemic administration. It is understood that these dosage ranges are by way of example only, and that daily administration can be adjusted depending on the factors listed above.

A preferred method of systemic administration is oral. Individual doses of from about 10 mg to about 1000 mg, preferably from about 10 mg to about 300 mg, are preferred.

Topical administration can be used to deliver the Formula (I) compound systemically, or to treat a subject locally. The amounts of Formula (I) compound to be topically administered depends upon such factors as skin sensitivity, type and location of the tissue to be treated, the composition and carrier (if any) to be administered, the particular Formula (I) compound to be administered, as well as the particular disorder to be treated and the extent to which systemic (as distinguished from local) effects are desired.

The compounds of the present invention can be targeted to specific locations within the body by using targeting ligands well known in the art. For example, to focus a Formula (I) compound to ischemic cardiac tissue, the compound is conjugated to an antibody or fragment thereof which is irmunoreactive with a cardiac cell marker as is broadly understood in the preparation of immunopharmraceuticals in general. The targeting ligand can also be a ligand suitable for a receptor that is present on the cardiac tissue. Any targeting ligand that specifically reacts with a marker for the intended target tissue can be used. Methods for coupling the invention compound to the targeting ligand are well known and are similar to those described below for coupling to a carrier. The conjugates are formulated and administered as described above.

For localized conditions, topical administration is preferred. For example, to treat a non-healing skin lesion, the compound is applied locally and topically, in a gel, paste, salve or ointment. For treatment of oral diseases, such as gingivitis, the compound may be applied locally in a gel, paste, mouth wash, or implant. The mode of treatment thus reflects the nature of the condition and suitable formulations for any selected route are available in the art.

In all of the foregoing, of course, the compounds of the invention can be administered alone or as mixtures, and the compositions may further include additional drugs or excipients as appropriate for the indication.

VII. Examples—Compound Preparation:

EXAMPLES 1–20

The following chart shows the structure of compounds made according to the procedures described in Examples 1–20.

TABLE I

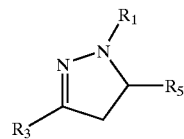

Formula (I)

| Example | R1 | R3 | R5 | EC$_{50}$[1] |
|---|---|---|---|---|
| 1. | phenyl | 2-pyridyl | phenyl | 23 |
| 2. | 2-pyridyl | phenyl | phenyl | 6 |
| 3. | 2-pyridyl | 2-hydroxyphenyl | phenyl | 1.7 |
| 4. | 1-benzothiazole | 2-hydroxyphenyl | phenyl | 27 |
| 5. | 2-pyridyl | 2-hydroxyphenyl | p-toluyl | 5.7 |
| 6. | 2-pyridyl | 2-hydroxyphenyl | p-methoxyphenyl | 5.68 |
| 7. | 2-pyridyl | 2-hydroxyphenyl | o-methoxyphenyl | 5.5 |
| 8. | 2-pyridyl | 2-hydroxyphenyl | 2-pyridyl | 5.4 |
| 9. | 2-pyridyl | 2-hydroxyphenyl | o-hydroxyphenyl | 5.4 |
| 10. | methyl | 2-hydroxyphenyl | 2-pyridyl | 92 |
| 11. | methyl | 2-hydroxyphenyl | 1-thiazole | 12 |
| 12. | 2-hydroxyethyl | 2-hydroxyphenyl | 2-pyridyl | 65 |
| 13. | 2-cyanoethyl | 2-hydroxyphenyl | 2-pyridyl | 18 |
| 14. | p-toluyl | 2-pyridyl | phenyl | 2 |
| 15. | p-bromophenyl | 2-pyridyl | phenyl | 6.3 |
| 16. | phenyl | 2-pyridyl | m-chlorophenyl | 1.7 |
| 17. | phenyl | phenyl | p-dimethyl-aminophenyl | 6 |
| 18. | methyl | 3-naphthyl | p-methoxyphenyl | 11 |
| 19. | methyl | 3-naphthyl | p-fluorophenyl | 3.6 |
| 20. | methyl | 3-naphthyl | p-trifluoro-methylphenyl | 13 |

[1] EC$_{50}$ is the concentration of compound that induces the production of an amount of VEGF equal to half the maximum amount of VEGF induced by that compound.

Compounds are analyzed using $^1$H and $^{13}$C NMR obtained on a Varian Unity plus 300 MHz spectrometer, chemical shifts are reported in δ ppm downfield from TMS as an internal standard. The compounds are also analyzed using elemental analysis, mass spectra using a Fisons Platform-II quadrupole mass spectrometer, high resolution mass spectra and/or IR spectra as appropriate. Thin layer chromatography (hereinafter "TLC") analysis is performed on glass mounted silica gel plates (200–300 mesh; Baker or Analtech) with fluorescent indicator and visualized using UV detection.

Example 1

2-(1,5-Diphenyl-4,5-dihydro-1H-pyrazol-3-yl)-pyridine

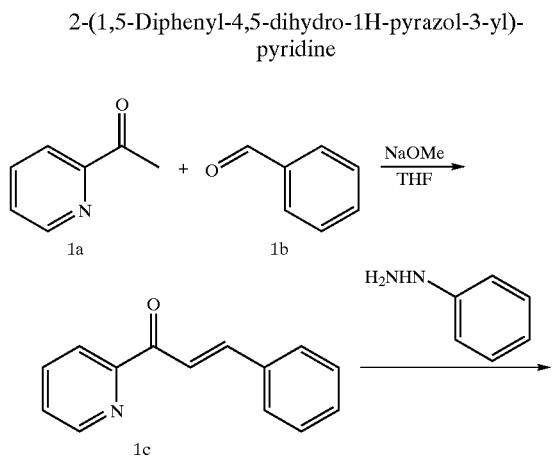

3-Phenyl-1-pyridin-2-yl-propenone (1c).

Method A: To solution of 2-acetylpyridine 1a (10 mmol, 1 equiv.) and tetrahydrofuran (25 mL) is added benzaldehyde 1b (10 mmol, 1 equiv.). Sodium methoxide (12 mmol, 1.2 equiv.) in methanol (24 mL, 0.5M) is introduced into the reaction and is agitated for 15 hours at room temperature. Hydrochloric acid (1N) is added until a neutral pH is obtained. The solution is extracted with dichloromethane twice, and washed once with water. The combined organic layers are dried over MgSO$_4$, and concentrated under reduced pressure. The residue is purified by flash column chromatography on SiO$_2$ (33% ethyl acetate/hexanes) to give the 3-phenyl-1-pyridin-2-yl-propenone 1c as a pale yellow solid. See Hollinshead, S. P., *Tetrahedron Letters*, Vol 37, pp. 9157–9160 (1996).

Method B: A solution of NaOH (12.8 mmol, 1.28 equiv.) in water (4.55 g) and ethanol (2.32 g) are introduced into a round bottom flask with a magnetic stirrer. Into the alkaline solution is placed 2-acetyl pyridine 1a (10 mmol, 1 equiv.) and the flask is rapidly surrounded by ice and the stirrer is started. The temperature reaches 10° C.–15° C. and benzaldehyde 1b (10 mmol, 1 equiv.) is added at once. The ice bath is removed and the reaction is stirred for 15 hours. The reaction is filtered. The filtrate is concentrated under reduced pressure and the product is purified by flash column chromatography on SiO$_2$ (33% ethyl acetate/hexanes) to give the 3-phenyl-1-pyridin-2-yl-propenone 1c as a pale yellow solid. See Kohler, E. P. & H. M. Chadwell, H. M., *Org. Synth., Coll*. Vol. 1, 2$^{nd}$ ed., p. 78.

2-(1,5-Diphenyl-4,5-dihydro-1H-pyrazol-3-yl)-pyridine (1d).

To a solution of a 3-phenyl-1-pyridin-2-yl-propenone 1c (0.10 mmol, 1 equiv.) in ethanol (4 mL), is added phenyl hydrazine free base (0.10 mmol, 1 equiv.) and sodium hydroxide (0.10 mmol, 1 equiv.). The mixture is stirred at 60° C. for 8 hours (temperature and reaction time can vary, higher temperature if in a sealed system). Water and ethyl acetate is added to the reaction and the phases are separated. The organic layer is washed until the water runs clear, and the aqueous layer is extracted with ethyl acetate two times. The combined organic layer is dried over Na$_2$SO$_4$, decanted and concentrated under reduced pressure. The residue is purified by high pressure liquid chromatography (Gilson HPLC, 5%–95% methanol in water, 9 minute gradient, 210 nm), and concentrated under reduced pressure to afford 2-(1,5-diphenyl-4,5-dihydro-1H-pyrazol-3-yl)-pyridine 1d as a yellow powder. Powers, D. G., et al,. *Tetrahedron*, Vol. 54, pp. 4085–4096 (1998).

Example 2

2-(3,5-Diphenyl-4,5-dihydro-pyrazol-1-yl)-pyridine

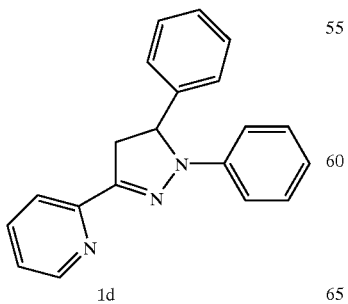
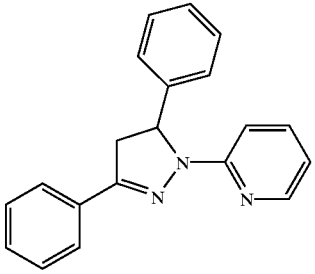

Example 2 is prepared using 1-acetylbenzene and benzaldehyde (method A) to afford 1,3-diphenyl-propenone.

The propenone is reacted with 2-hydrazinopyridine following the procedure described for Example 1.

Example 3

2-(5-Phenyl-1-pyridin-2-yl-4,5-dihydro-1H-pyrazol-3-yl)-phenol

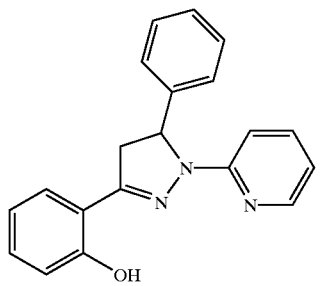

Example 3 is prepared using 2-hydroxychalcone and 2-hydrazinopyridine following the procedure described for Example 1.

Example 4

2-(1-Benzothiazol-2-yl-5-phenyl-4,5-dihydro-1H-pyrazol-3-yl)-phenol

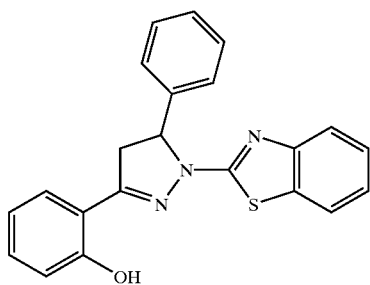

Example 4 is prepared using 2-hydroxychalcone and benzothiazol-2-yl-hydrazine following the procedure described for Example 1.

Example 5

2-(1-Pyridin-2-yl-5-p-tolyl-4,5-dihydro-1H-pyrazol-3-yl)-phenol

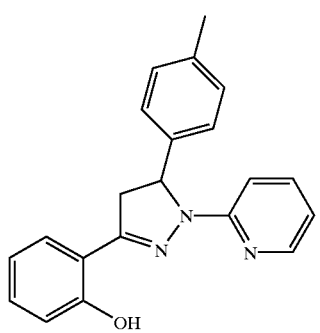

Example 5 is prepared using 1-(2-hydroxy-phenyl)-3-p-tolyl-propenone and 2-hydrazinopyridine following the procedure described for Example 2.

Example 6

2-[5-(4-Methoxy-phenyl)-1-pyridin-2-yl-4,5-dihydro-1H-pyrazol-3-yl]-phenol

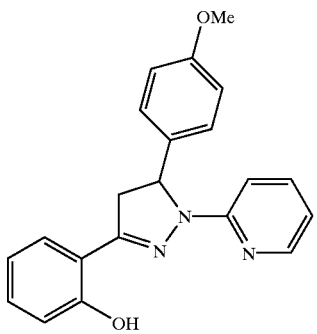

Example 6 is prepared using 1-(2-hydroxy-phenyl)-3-p-methoxy-propenone and 2-hydrazinopyridine following the procedure described for Example 2.

Example 7

2-[5-(2-Methoxy-phenyl)-1-pyridin-2-yl-4,5-dihydro-1H-pyrazol-3-yl]-phenol

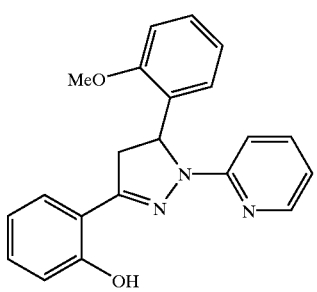

Example 7 is prepared using 1-(2-hydroxy-phenyl)-3-o-methoxy-propenone and 2-hydrazinopyridine following the procedure described for Example 2.

Example 8

2-(1,5-Di-pyridin-2-yl-4,5-dihydro-1H-pyrazol-3-yl)-phenol

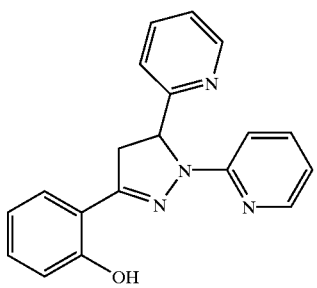

Example 8 is prepared using 2-acetylbenzene and 2-pyridinecarboxaladehyde (method A) to afford 1-(2-hydroxy-phenyl)-3-pyridin-2-yl-propenone. The propenone is reacted with 2-hydrazinopyridine following the procedure described for Example 1.

Example 9

2-[5-(2-hydroxy-phenyl)-1-pyridin-2-yl-4,5-dihydro-1H-pyrazol-3-yl]-phenol

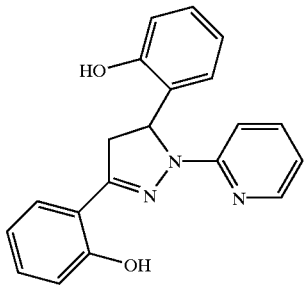

Example 9 is prepared using 2-acetylbenzene and 2-salicylaldehyde (method A) to afford 1,3-bis-(2-hydroxy-phenyl)-propenone. The propenone is reacted with and 2-hydrazinopyridine following the procedure described for Example 1.

Example 10

2-(1-Methyl-5-pyridin-2-yl-4,5-dihydro-1H-pyrazol-3-yl)-phenol

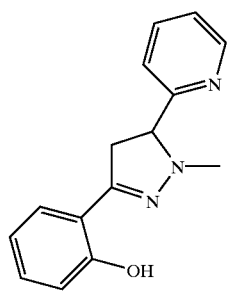

Example 10 is prepared using 1-(2-hydroxy-phenyl)-3-pyridin-2-yl-propenone and methylhydrazine following the procedure described for Example 1.

Example 11

2-(1-Methyl-5-thiazol-2-yl-4,5-dihydro-1H-pyrazol-3-yl)-phenol

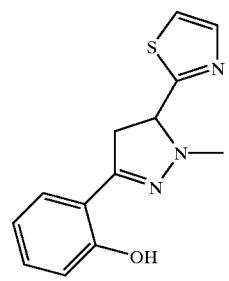

Example 11 is prepared using 2-acetylbenzene and thiazole-2-carbaldehyde (method A) to afford 1-(2-hydroxy-phenyl)-3-thiazol-2-yl-propenone. The propenone is reacted with methylhydrazine following the procedure described for Example 1.

Example 12

2-[1-(2-Hydroxy-ethyl)-5-pyridin-2-yl-4,5-dihydro-1H-pyrazol-3-yl]-phenol

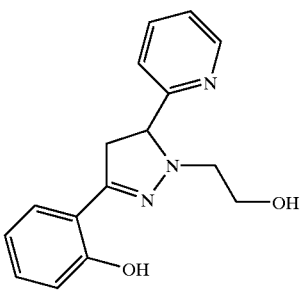

Example 12 is prepared using 1-(2-hydroxy-phenyl)-3-pyridin-2-yl-propenone and 2-hydrazino-ethanol following the procedure described for Example 1.

Example 13

3-[3-(2-Hydroxy-phenyl)-5-pyridin-2-yl-4,5-dihydro-pyrazol-1-yl]-propionitrile

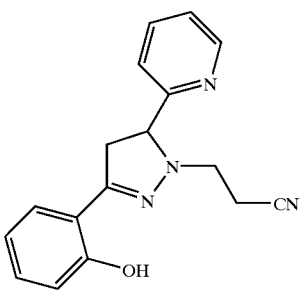

Example 13 is prepared using 1-(2-hydroxy-phenyl)-3-pyridin-2-yl-propenone and 3-hydrazino-propionitrile following the procedure described for Example 1.

Example 14

2-(5-Phenyl-1-p-tolyl-4,5-dihydro-1H-pyrazol-3-yl)-pyridine

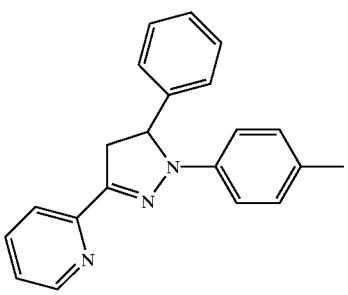

Purchased from Sigma.

Example 15

2-[1-(4-Bromo-phenyl)-5-phenyl-4,5-dihydro-1H-pyrazol-3-yl]-pyridine

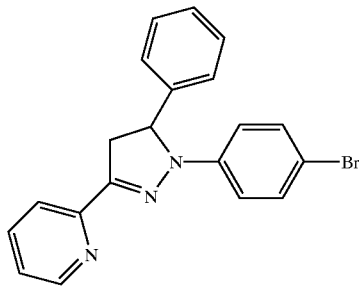

Purchased from Sigma.

Example 16

2-[5-(3-Chloro-phenyl)-1-phenyl-4,5-dihydro-1H-pyrazol-3-yl]-pyridine

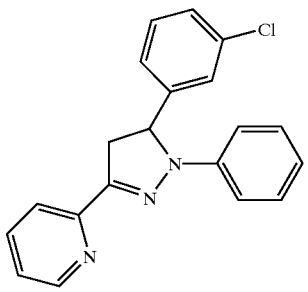

Purchased from Sigma.

Example 17

[4-(2,5-Diphenyl-3,4-dihydro-2H-pyrazol-3-yl)-phenyl]-dimethyl-amine

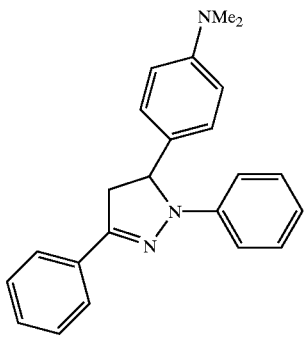

Purchased from Sigma.

Example 18

5-(4-Methoxy-phenyl)-1-methyl-3-naphthalen-2-yl-4,5-dihydro-1H-pyrazole

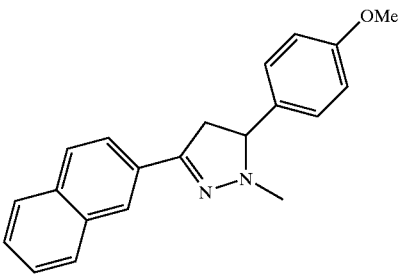

Purchased from Maybridge.

Example 19

5-(4-Fluoro-phenyl)-1-methyl-3-naphthalen-2-yl-4,5-dihydro-1H-pyrazole

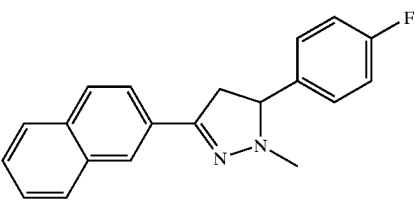

Purchased from Maybridge.

Example 20

1-Methyl-3-naphthalen-2-yl-5-(4-trifluoromethyl-phenyl)-4,5-dihyaro-1H-pyrazole

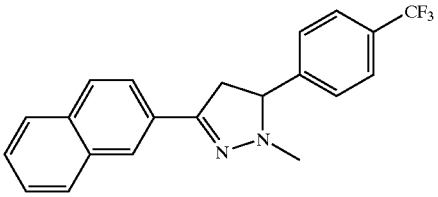

Purchased from Maybridge.

VIII. Examples—Methods of Screening Compounds.

A compound of Formula (I) can be screened for the appropriate therapeutic use in a number of different ways. The following assays also may be used to optimize therapeutic doses of the compounds. In turn, toxicity would be established according to standard tests well known in the art for determination of compound toxicity.

Examples I–VI teach methods of screening compounds appropriate for the therapeutic goal of increasing vascularzation of tissue. Although the following examples may focus on the HIF-1 target gene VEGF as a well known mediator of angiogenesis, one skilled in the art will appreciate that these, and other methods, can be readily adapted to screen the compounds of Formula (I) to other HIF-1 target genes as well as other therapeutic goals. Indeed, given that compounds increase the biological activity of a transcription factor, HIF-1 controls the expression of multiple genes involved in angiogenesis and thus will presumably give a superior clinical outcome compared to treatment with a single angiogenic factor such as VEGF. On the other hand, if the therapeutic goal is to increase EPO, these methods can be adapted to screen for compounds of Formula (I) that increase the transcription of EPO.

Example I details a VEGF-luciferase reporter gene assay that measures a compound's ability to stimulate transcription of a luciferase gene linked to an upstream VEGF promoter-enhancer sequence. Example II details an enzyme-linked immunosorbancy assay (ELISA) for VEGF that measures the ability of a compound of the present invention to stimulate secretion of VEGF from a cell. Example III details a gene panel assay. Messenger RNA for eight different genes is measured from a cell line that is treated with a compound of the present invention. Example IV details an immunoblot assay for the induction of HIF-1. Example V details the effect the compounds of the present invention have upon increased amount of VEGF in rat cardiac tissue. Example VI details the level of EPO in blood after rats are treated with the compounds of the present invention.

EXAMPLE I

Any compound of the present invention can be screened by a VEGF-luciferase assay. The assay evaluates the transcriptional activity of the compounds. A VEGF-luciferase cell line is prepared in a ELEM parental line as described in Engelmann, G. L., et al., "Formation of fetal rat cardiac cell clones by retroviral transformation: retention of select myocyte characteristics", *J. Mol. Cell. Cardio.*, Vol. 25, pp. 2979–84 (1998). ELEM cells are v-H-ras transformed neonatal rat ventricular cardiomyocytes. A luciferase reporter plasmid is constructed using the pGL2-basic (Promega) plasmid containing an insert consisting of 2.65 kb of the vegf promoter (bp −2274 to +379 relative to the transcription initiation site) fused to the firefly luciferase coding sequences as well as SV40 intron and polyadenylation signals. This reporter plasmid, along with a control plasmid containing an SV40-neomyocin and Cytomeagalovirus (CMV)-βgal construct, are transfected into ELEM cells and stable transfectants are selected in G418. Responses of the VEGF-luciferase reporter to hypoxia and to desferoximine, a mimetic of hypoxic responses, are tested, and a clone with strong and reproducible responses are selected. ELEM cells and their transfectants are grown in Dulbecco's Modified Eagle's Medium/F12 (1:1) (Life Technologies) that include 10% heat-inactivated fetal bovine serum, unless otherwise indicated (Life Technologies), a 1× penicillin/streptomysin mixture (Life Technologies) and 500 µg/ml G418 (Life Technologies). Tissue culture plates are precoated with fibronectin. The standard condition for assaying is established as follows: cells are plated in 96-well plates at a density of 6×10³ cells per well in 100 µl of media per well. 42 hrs later, compounds are added to the wells in 10 µl aliquots. Six hours after addition of compounds, cells are lysed and assayed for luciferase and β-galactosidase activity. Compounds for pharmaceutical use are selected based upon cells exhibiting the greatest luciferase and β-galactosidase activity.

EXAMPLE II

Any compound of the present invention can be screened by a VEGF-ELISA assay. VEGF secretion is assayed in the HL-1 cardiomyocyte cell line as described in Claycomb, W. C., "HL-1 cells: a cardiac muscle cell line that contracts and retains phenotypic characteristics of the adult cardiomyocyte", *Proc. Natl. Acad. Sci U.S.A.*, Vol. 95, pp. 2979–84 (1998). For experiments, HL-1 cells are plated in 96-well plates at a density of $2 \times 10^4$ cells per well in growth medium: EXCEL 320 media (JRH Biosciences, Lenexia, Kans.) plus 10% fetal bovine serum (BioWhitaker), 100 nM retinoic acid (Sigma, St. Louis, Mo.), 10 µM norepinephrine (Sigma), 10 µg/ml insulin (Life Technologies, Grand Island, N.Y.), 1× non-essential amino acid supplement (Life Technologies), 50 µg/ml endothelial cell growth supplement (Upstate Biotechnology, Lake Placid, N.Y.), 100 units/ml penicillin, 100 units/ml streptomycin (Life Technologies). After 24 hrs, the media is replaced with a low-growth media (HL-1 media with 2% fetal bovine serum and without endothelial cell growth supplement) containing test compounds with 0.5% dimethyl sulfoxide (DMSO). After 18 hrs, conditioned media from the treated cells was assayed for VEGF content with a Murine VEGF-ELISA kit (R&D Systems, Minneapolis, Minn.). The amount of VEGF secreted into the media over an 18 hr period is normalized to positive control wells which are treated with a maximally effective concentration (1 mM) of deferoxamine mesylate (Sigma, St. Louis) and are reported as "percent activity," where the VEGF in unstimulated wells is defined as 0% and the VEGF in wells treated with 1 mM deferoxamine is defined as 100%. Potency is determined by stimulating cells with 10 concentrations of test compounds (200 nM to 100 µM) and fitting the data to a variable slope sigmoidal dose-response curve using GraphPad Prism version 3.00 for Windows 95 (GraphPad Software, San Diego, Calif.). Determinations for each test compound are performed in three separate experiments and the means±standard deviation of the $Log(EC_{50})$ and maximum response are evaluated. Compounds for pharmaceutical use are selected based upon the greatest percent activity.

EXAMPLE III

Any compound of the present invention can be screened by a gene selectivity panel assay to determine the specificity of induction of VEGF. Messenger RNA for eight genes expressed in HL-1 cells is quantified using real-time reverse transcriptase-polymerase chain reaction (TaqMan) in duplex reactions using β-actin as a control reference gene as described in Heid, C. A., et al., "Real time quantitative PCR", *Genome Res.*, Vol. 6, pp.986–994 (1996). HL-1 cells are treated for 18 hr with test compounds at concentrations equal to 10 times the $EC_{50}$, and total RNA is prepared using TriReagent (Molecular Research Center, Cincinnati, Ohio). Polymerase Chain Reaction (PCR) primers specific to each gene of the panel are designed to span introns where possible and are generated using the Primer Express™ Oligo Design Software System (Applied Biosystems) and compared with sequences in the GenBank database to eliminate cross-hybridization with other genes. All TaqMan probes designed against target genes are 5'-labeled with 6-FAM (6-carboxy-fluorescein) reporter dye and 3'-labeled with TAMRA (6-carboxy-tetramethyl-rhodamine) quencher dye (see Table II). The TaqMan® probe specific for the β-actin control gene are 5'-labeled with VIC (Applied Biosystems) reporter dye (see Table II) to enable dual amplification and resolution of target and control products in the same reaction for normalization. Primers and probe monocyte chemoattractant protein-1 (MCP-1) are from Applied Biosystems sold as TaqMan® PDAR Target Reagents.

Primer concentrations are optimized to ensure that both genes in each reaction are amplified with equal efficiencies and that primers for one gene do not affect the efficiency of amplification of the other. All genes are amplified in a reaction mixture containing 15 ng RNA, 3.12 mM manganese acetate, 1.25 mM deoxyadenine triphosphate (dATP), deoxycytidine triphosphate (dCTP), deoxyguanidine triphosphate (dGTP), 2.5 mM deoxyuridine triphosphate (dUTP), 2.5 units rTth DNA Polymerase, 1 unit AmpErase UNG, 150 gene. ΔΔ-CT levels can be converted to a percent change according to the relationship "$100 \times 2^{-(\Delta\Delta Ct)}=\%$ change. Compounds for pharmaceutical use are selected based on having a high % change in VEGF or GAPDH expression and low % change for the non-hypoxia regulated genes.

TABLE II

| Gene | Primer Sequences (5' to 3') | | Probe Sequence (5' to 3') | | Probe Dye |
|---|---|---|---|---|---|
| VEGF | Forward: ACCCTGGCTTTACTGCTGTACCT | (SEQ ID NO:1) | ACCATGCCAAGTGGTCCCAGGC | (SEQ ID NO:3) | FAM |
| | Reverse: TGGGACTTCTGCTCTCCTTCTG | (SEQ ID NO:2) | | | |
| SERCA | Forward: GTAGACAGATGTTGGTGCAATACAAGTA | (SEQ ID NO:4) | ACTACAGTCAAACATGCGCTGTGAGAAGCTG | (SEQ ID NO:6) | FAM |
| | Reverse: CAATACCTGTTACCAGCACAGAAACT | (SEQ ID NO:5) | | | |
| TGF-β1 | Forward: GCTCTTGTGACAGCAAAGATAACAA | (SEQ ID NO:7) | CCACGTGGAAATCAACGGGATCAGC | (SEQ ID NO:9) | FAM |
| | Reverse: GGTCGCCCCGACGTTT | (SEQ ID NO:8) | | | |
| ANP | Forward: TGCGGTGTCCAACACAGATC | (SEQ ID NO:10) | ATGGATTTCAAGAACCTGCTAGACCACCTGG | (SEQ ID NO:12) | FAM |
| | Reverse: GCTTCCTCAGTCTGCTCACTCA | (SEQ ID NO:11) | | | |
| β-MHC | Forward: GTGCCAAGGGCCTGAATG | (SEQ ID NO:13) | CCCAGCTCTAAGGGTGCCCGTGAA | (SEQ ID NO:15) | FAM |
| | Reverse: CACCTAAAGGGCTGTTGCAAA | (SEQ ID NO:14) | | | |
| α-MHC | Forward: GGAGGAGAGGGCGGACAT | (SEQ ID NO:16) | ATGTCCCGGCTCTTGGCCCG | (SEQ ID NO:18) | FAM |
| | Reverse: AGAGGTTATTCCTCGTCGTGCAT | (SEQ ID NO:17) | | | |
| GAPDH | Forward: TGCACCACCAACTGCTTAG | (SEQ ID NO:19) | CAGAAGACTGTGGATGGCCCCTC | (SEQ ID NO:21) | FAM |
| | Reverse: GGATGCAGGGATGATGTTC | (SEQ ID NO:20) | | | |
| MCP-1 | proprietary (Applied Biosystems) | | proprietary (Applied Biosystems) | | FAM |
| β-actin | Forward: GTCCACCTTCCAGCAGATGTG | (SEQ ID NO:22) | CAGGAGTACGATGAGTCCGGCCCC | (SEQ ID NO:24) | VIC |
| | Reverse: CAGTCCGCCTAGAAGCACTTG | (SEQ ID NO:23) | | | | nM target probe and 150 nM β-actin probe. VEGF, transforming growth Factor-β 1 (TGF-β1), sarcolemal endoplasmic reticulum calcium ATPase (SERCA), angiopoietin-1 (Ang-1), and β-myosin heavy chain (β-MHC) RNA are each amplified in separate reactions containing the reaction mixture as previously described as well as 300 nM forward and reverse target primers and 60 nM β-actin forward and reverse primers. Glyceraldehyde phosphate dehydrogenase (GAPDH), α-myosin heavy chain (α-MHC), and atrial natriuretic peptide (ANP) are each amplified in separate reactions containing the reaction mixture as previously described as well as 80 nM forward and reverse target primers and 60 nM β-actin forward and reverse primers. MCP-1 is amplified using a 20× primer and probe stock solution prepared and supplied by Applied Biosystems and is used as 1× in the PCR reaction. PCR Thermal cycling for all reactions is 50° C.×2 min, 60° C.×30 min, 95° C.×5 min, followed by 40 cycles of 94° C.×20 seconds and 62° C.×1 min.). Raw Cycle Threshold (CT) values for each target gene are calculated by the Sequence Detection Software (Applied Biosystems). Each target gene level is then compared relative to the β-actin level in that same sample by subtracting the CT for β-actin from the CT for the target gene to arrive at a Δ-CT level. In turn, Δ-CT levels for treated samples are then subtracted from Δ-CT level of vehicle treated samples to arrive at a ΔΔ-CT level for that

EXAMPLE IV

Any compound of the present invention can be screened by an immunoplot assay for the HIF-1α protein. HEK-293 cells are treated with test compounds for 2 to 18 hrs and nuclear and cytoplasmic extracts are made. Cells are lysed at 4C in a lysis buffer consisting of: 10 mM Tris HCl, pH 7.4, 10 mM NaCl, 3 mM $MgCl_2$, 0.5% Np-40, and containing protease inhibitors: 10 mM NaF, 1 mM PMSF, 2 µg/ml leupeptin, 2 µg/ml pepstatin, 2 mM sodium orthovanadate and crude cytoplasmic fractions were removed. Nuclear pellets were extracted for 20 min at 4 C in 20 mM HEPES, pH 7.9, 1 mM EDTA 420 mM NaCl, and 20% glycerol with protease inhibitors and the supernatants are collected following centrifugation for 15 min at 10,000×g. Protein concentration of extracts are measured using a BCA Assay Kit (Pierce, Rockford, Ill.) and 10 µg of each is run on a 10% acrylamide Tris-glycine gel (Novus Biologicals, Littleton Colo.), transferred to nitrocellulose membranes and probed with a monoclonal antibody to human HIF-1α (BD Transduction Labs, Lexington, Ky.). Compounds for pharmaceutical use are selected based on an 140 kDalton protein recognized by the anti-HIF-1α antibody.

EXAMPLE V

Any compound of the present invention can be screened by measuring the amount of VEGF protein in cardiac tissue after treatment. Sprague Dawley rats are treated with IV infusions of a test compound for 6 to 12 hr. Animals are euthanized by exsanguinations. Hearts are removed and frozen in liquid $N_2$. To extract VEGF, pieces of cardiac tissue are homogenized on ice in 10 mM Tris, 2 mM MgCl2, 150 mM NaCl, 1% triton X-100 and protease inhibitors (Complete™ Proteinase Inhibitors, Boehringer Manheim). Aliquots of the crude homogenate are sonicated and centrifuged at 11,000×g for 10 min at 4° C. The supernates are analyzed for VEGF content using a ELISA kit (R&D Systems). Total protein concentration of the crude homogenate is also determined using a BCA Assay kit (Pierce). Final VEGF levels are expressed as a percentage of extractable VEGF per mg of protein. Compounds for pharmaceutical use are selected based on highest percentages.

EXAMPLE VI

Any compound of the present invention can be screened by measuring the amount of EPO in serum. After the compounds are administered to Spraque-Dawley rats, blood is drawn and allowed to clot in polypropylene tubes for 2 hrs at room temperature. Clotted blood is precipitated by centrifugation and serum supernates are collected and analyzed using an EPO-Trac™ $^{125}$I Radioimmunoassay Kit (Diasorin, Stillwater, Minn.) according to the instruction protocol provided. Prior to analysis, serum samples are diluted 1:4 or 1:8 in EPO-Trac standard buffer. Final values are corrected to account for the dilution. Compounds for pharmaceutical use are selected based on their ability to induce the highest plasma EPO values.

It is contemplated that not only are the present examples non-limiting, but also may be used in combination to select a compound of the present invention to the desired therapeutic goal(s) such as increasing vascularization of tissue in a subject. To this end, a compound that is found to induce the VEGF-luciferase reporter of Example I can be tested in the VEGF-ELISA assay of Example II to determine if the compound stimulates VEGF protein production from an endogenous VEGF gene. Further, the compound can then be tested in the gene selectivity panel assay of Example III to assess the specificity of the response. Further still, the compound can be assessed in the immunoblot assay for HIF-1 of Example IV to determine if the compound increases HIF-1. Further even still, the compound can be further tested in vivo for its ability to increase VEGF protein expression in rat tissue of Example V or increase EPO protein levels in rat serum of Example VI.

IX. Examples—Compositions and Methods of use:

The compounds of the invention are useful to prepare compositions for the treatment of ailments associated with hypoxia. The following composition and method examples do not limit the invention, but provide guidance to the skilled artisan to prepare and use the compounds, compositions and methods of the invention. The skilled practitioner will appreciate that the examples may be varied based on the condition being treated and the patient.

EXAMPLE A

A tablet composition for oral administration, according to the present invention, is made comprising:

| Component | Amount (mg per tablet) |
| --- | --- |
| Compound of Example 3 | 5 |
| Microcrystalline Cellulose | 100 |

-continued

| Component | Amount (mg per tablet) |
| --- | --- |
| Sodium Starch Glycollate | 30 |
| Magnesium Stearate | 3 |

When administered orally once daily, the above composition substantially increases EPO in a subject suffering from anemia.

EXAMPLE B

A capsule for oral administration, according to the present invention, is made comprising:

| Component | Amount (% w/w) |
| --- | --- |
| The compound of Example 14 | 15% |
| Polyethylene glycol | 85% | wherein 1.5 grams of the compound is placed in a standard gelatin capsule.

A human subject suffering from angina is treated by a method of this invention. With a regimen of three capsules per day administered orally to the subject, the patient's angina is relieved. At the end of the treatment period, the subject is examined and is found to have increased vascularization to the once ischemic cardiac tissue.

EXAMPLE C

A topical composition for local administration, according to the present invention, is made comprising:

| Component | Composition (% w/v) |
| --- | --- |
| The compound of Example 16 | 0.20 |
| Benzalkonium chloride | 0.02 |
| Thimerosal | 0.002 |
| d-Sorbitol | 5.00 |
| Glycine | 0.35 |
| Sensates, including oil of wintergreen | 0.075 |
| Purified water | q.s. |
| Total = | 100.00 |

A diabetic subject suffering from a non-healing wound applies the topical to the wound twice a day. After one month, the wound is substantially healed.

While particular embodiments of the subject invention have been described, it would be apparent to those skilled in the art that various changes and modifications to the compositions disclosed herein can be made without departing from the spirit and scope of the invention. It is intended to cover, in the appended claims, all such modifications that are within the scope of this invention.

What is claimed is:

1. A compound having the following structure:

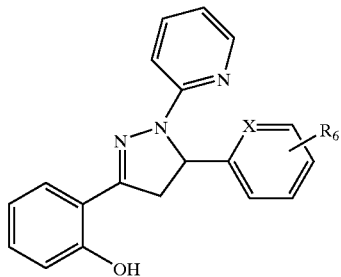

characterized in that:
(a) X is selected from CH;
(b) R6 is selected from the group consisting of nil, methyl, ethyl, methoxy, ethoxy, amino and halo;
or an optical isomer, diastereomer or enantiomer, or pharmaceutically-acceptable salt, or biohydrolyzable amide, ester, or imide thereof.

2. The compound of claim 1, wherein the compound is selected from the group consisting of 2-(5-Phenyl-1-pyridin-2-yl-4,5-dihydro-1H-pyrazol-3-yl)-phenol, 2-(1-Pyridin-2-yl-5-p-tolyl-4,5-dihydro-1H-pyrazol-3-yl)-phenol, 2-[5-(4-Methoxy-phenyl)-1-pyridin-2-yl-4,5-dihydro-1H-pyrazol-3-yl]-phenol, 2-[5-(2-Methoxy-phenyl)-1-pyridin-2-yl-4,5-dihydro-1H-pyrazol-3-yl]-phenol, and 2-[5-(2-hydroxy-phenyl)-1-pyridin-2-yl-4,5-dihydro-1H-pyrazol-3-yl]-phenol.

3. A pharmaceutical composition in unit dosage form comprising:
(a) a safe and effective amount of a compound having the structure:

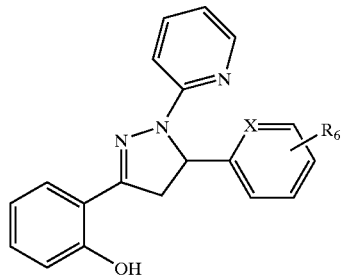

characterized in that:
a. X is selected from CH;
b. R6 is selected from the group consisting of nil, methyl, ethyl, methoxy, ethoxy, amino and halo; or an optical isomer, diastereomer or enantiomer, or pharmaceutically-acceptable salt, or biohydrolyzable amide, ester, or imide thereof; and
(b) a pharmaceutically-acceptable carrier.

4. The pharmaceutical composition of claim 2, wherein the compound is selected from the group consisting of 2-(5-Phenyl-1-pyridin-2-yl-4,5-dihydro-1H-pyrazol-3-yl)-phenol, 2-(1-Pyridin-2-yl-5-p-tolyl-4,5-dihydro-1H-pyrazol-3-yl)-phenol, 2-[5-(4-Methoxy-phenyl)-1-pyridin-2-yl-4,5-dihydro-1H-pyrazol-3-yl]-phenol, 2-[5-(2-Methoxy-phenyl)-1-pyridin-2-yl-4,5-dihydro-1H-pyrazol-3-yl]-phenol, and 2-[5-(2-hydroxy-phenyl)-1-pyridin-2-yl-4,5-dihydro-1H-pyrazol-3-yl]-phenol.

* * * * *

UNITED STATES PATENT AND TRADEMARK OFFICE
CERTIFICATE OF CORRECTION

PATENT NO.    : 6,878,729 B2
DATED         : April 29, 2002
INVENTOR(S)   : Ji-In Kim Almstead et al.

It is certified that error appears in the above-identified patent and that said Letters Patent is hereby corrected as shown below:

<u>Column 8,</u>
Line 6, delete "Punne" and insert -- Purine --.
Line 56, delete "Spiro" and insert -- spiro --.

<u>Column 9,</u>
Line 66, delete "Coumann" and insert -- Coumarin --.

<u>Column 12,</u>
Line 47, delete "one" and insert -- enone --.

<u>Column 17,</u>
Line 7, delete "conmmingled" and insert -- commingled --.

<u>Column 20,</u>
Line 29, delete "irmunoreactive" and insert -- immunoreactive --.

<u>Column 28,</u>
Line 38, delete "dihyaro" and insert -- dihydro --.

<u>Column 29,</u>
Line 10, delete "Example H" and insert -- Example II --.

<u>Column 33,</u>
Lines 8 and 23, delete "supemates" and insert -- supernates --.

UNITED STATES PATENT AND TRADEMARK OFFICE
CERTIFICATE OF CORRECTION

PATENT NO. : 6,878,729 B2
DATED : April 29, 2002
INVENTOR(S) : Ji-In Kim Almstead et al.

It is certified that error appears in the above-identified patent and that said Letters Patent is hereby corrected as shown below:

<u>Column 41,</u>
Lines 26 and 27, delete "selected from".

Signed and Sealed this

Twenty-eighth Day of March, 2006

JON W. DUDAS
*Director of the United States Patent and Trademark Office*

UNITED STATES PATENT AND TRADEMARK OFFICE
CERTIFICATE OF CORRECTION

PATENT NO.     : 6,878,729 B2
DATED           : April 12, 2005
INVENTOR(S)  : Ji-In Kim Almstead et al.

It is certified that error appears in the above-identified patent and that said Letters Patent is hereby corrected as shown below:

Column 8,
Line 6, delete "Punne" and insert -- Purine --.
Line 56, delete "Spiro" and insert -- spiro --.

Column 9,
Line 66, delete "Coumann" and insert -- Coumarin --.

Column 12,
Line 47, delete "one" and insert -- enone --.

Column 17,
Line 7, delete "conmmingled" and insert -- commingled --.

Column 20,
Line 29, delete "irmunoreactive" and insert -- immunoreactive --.

Column 28,
Line 38, delete "dihyaro" and insert -- dihydro --.

Column 29,
Line 10 , delete "Example H" and insert -- Example II --.

Column 33,
Lines 8 and 23, delete "supemates" and insert -- supernates --.

UNITED STATES PATENT AND TRADEMARK OFFICE
CERTIFICATE OF CORRECTION

PATENT NO. : 6,878,729 B2
DATED : April 12, 2005
INVENTOR(S) : Ji-In Kim Almstead et al.

It is certified that error appears in the above-identified patent and that said Letters Patent is hereby corrected as shown below:

Column 41,
Lines 26 and 27, delete "selected from".

This certificate supersedes Certificate of Correction issued March 28, 2006.

Signed and Sealed this

Second Day of May, 2006

JON W. DUDAS
*Director of the United States Patent and Trademark Office*